(12) United States Patent
Benscik-Reynier et al.

(10) Patent No.: US 7,566,530 B2
(45) Date of Patent: *Jul. 28, 2009

(54) METHOD FOR DETECTING PRP USING AT LEAST ONE POSITIVE CHARGE AND/OR AT LEAST ONE GLYCOSIDIC BOND AND A LIGAND OTHER THAN A PROTEIN LIGAND

(75) Inventors: Anna Benscik-Reynier, Saint Clair de la Tour (FR); Anthony William Coleman, Caluire et Cuire (FR); Eric Da Silva, Lyons (FR); Marilyne Dupin, Vaugneray (FR); Edwige Leclere, Lyons (FR); Ambroise Martin, Charly (FR); Aly Moussa, Oullins (FR); Herve Perron, Saint Genis les Ollieres (FR); Frederic Ronzon, Montromant (FR)

(73) Assignees: Biomerieux, Marcy l'Etoile (FR); Universite Claude Bernard Lyon, Villeubanne (FR); Centre National de la Recherche Scientifique, Paris (FR); Agence Francaise de Securite Sanit Aire des Aliments, Maisons-Alfort (FR)

( * ) Notice: Subject to any disclaimer, the term of this patent is extended or adjusted under 35 U.S.C. 154(b) by 331 days.

This patent is subject to a terminal disclaimer.

(21) Appl. No.: 10/583,891

(22) PCT Filed: Jan. 19, 2005

(86) PCT No.: PCT/FR2005/000118

§ 371 (c)(1),
(2), (4) Date: Jun. 22, 2006

(87) PCT Pub. No.: WO2005/080590

PCT Pub. Date: Sep. 1, 2005

(65) Prior Publication Data

US 2008/0176256 A1   Jul. 24, 2008

(30) Foreign Application Priority Data

Jan. 20, 2004   (FR) .................................. 04 00492
Jun. 17, 2004   (FR) .................................. 04 06538

(51) Int. Cl.
G01N 33/53   (2006.01)
C12Q 1/70   (2006.01)
C12P 19/54   (2006.01)
C12N 5/06   (2006.01)

(52) U.S. Cl. .............................. 435/5; 435/7.1; 435/81; 435/337

(58) Field of Classification Search ........................ None
See application file for complete search history.

(56) References Cited

U.S. PATENT DOCUMENTS 6,054,114 A * 4/2000 Lansbury et al. ............ 424/1.11
6,137,014 A * 10/2000 Godfried Andre Van Kruchten ............. 568/867

6,887,676 B1   5/2005 Collinge et al.
2002/0137114 A1   9/2002 Turecek et al.
2004/0096902 A1 * 5/2004 Kiesewetter et al. .......... 435/7.1
2006/0014215 A1 * 1/2006 Moussa et al. ............... 435/7.1

FOREIGN PATENT DOCUMENTS

| WO | WO 00/62068 A1 | 10/2000 |
|---|---|---|
| WO | WO 02/065133 A2 | 8/2002 |
| WO | WO 02/086511 A2 | 10/2002 |
| WO | WO 2004/059322 A1 | 7/2004 |
| WO | WO 2005/026740 A1 | 3/2005 |

OTHER PUBLICATIONS

Koga et al (2003) Chem. Eur. J. 9(5): 1146-1156.*

Da Silva et. al., "Synthesis and Solid-State Structures of Mono-Functionalised para-H-Calix-[6]-arenes," Journal of Supramolecular Chemistry, vol. 1, pp. 135-138, 2001.

Kumar et al., "The First Analogues of LNA (Locked Nucleic Acids): Phosphorothioate-LNA and 2'-Thio-LNA," Bioorganic & Medicinal Chemistry Letters 8, pp. 2219-2222, 1998.

Egholm et al., "Peptide Nucleic (PNA). Oligonucleotide Analogues with an Achiral Peptide Backbone[1]," J. Am, Chem Soc., vol. 114, pp. 1895-1897, 1992.

Madec et al., "Portease-resistant prion protein in brain and lymphoid organs of sheep within a naturally scrapie-infected flock." Microbial Pathogenesis, vol. 28, pp. 353-362, 2000.

U. K. Laemmli, "Cleavage of structural Proteins during the Assembly of the Head of Bateriophage." Nature, vol. 227, pp. 680-685, Aug. 15, 1970.

Toulmé et al., "Les aptamères: des ligands et des catalyseurs oligonculéotidiques obtenus par sélecxtion in vitro," Médecine/Sciences, vol. 14, pp. 155-166, 1998.

Prusiner et al., "Scrapie Prions Aggregate to Form Amyloid-like Birefringent Rods," Cell., vol. 35, No. 2 Pt. 1, pp. 349-358, Dec. 1983.

Meyer et al., "Detection of Bovine Spongiform Encephalopathy-Specific $PrP^{Sc}$ by Treatment with Heat and Guanidine Thiocyanate," Journal of Virology, vol. E73, No. 11, pp. 9386-9392, Nov. 1999.

Da Silva et al., "Synthesis and complexation properties towards amino acids of mono-substituted p-sulphonato-calix-[n]-arenes," Tetrahedron, vol. 59, No. 37, pp. 7357-7364, Sep. 2003.

(Continued)

Primary Examiner—Gary B. Nickol
Assistant Examiner—Michelle Horning
(74) Attorney, Agent, or Firm—Oliff & Berridge, Plc.

(57) ABSTRACT

The invention relates to a method for detecting PrP in a biological human or animal sample that may contain PrP. The inventive method is characterised in that it uses a molecule containing at least one positive charge and/or at least one osidic bond and a ligand other than a proteinic ligand selected from macrocyclic ligands and glycosaminoglycanes.

12 Claims, 9 Drawing Sheets

OTHER PUBLICATIONS

Figure 1:
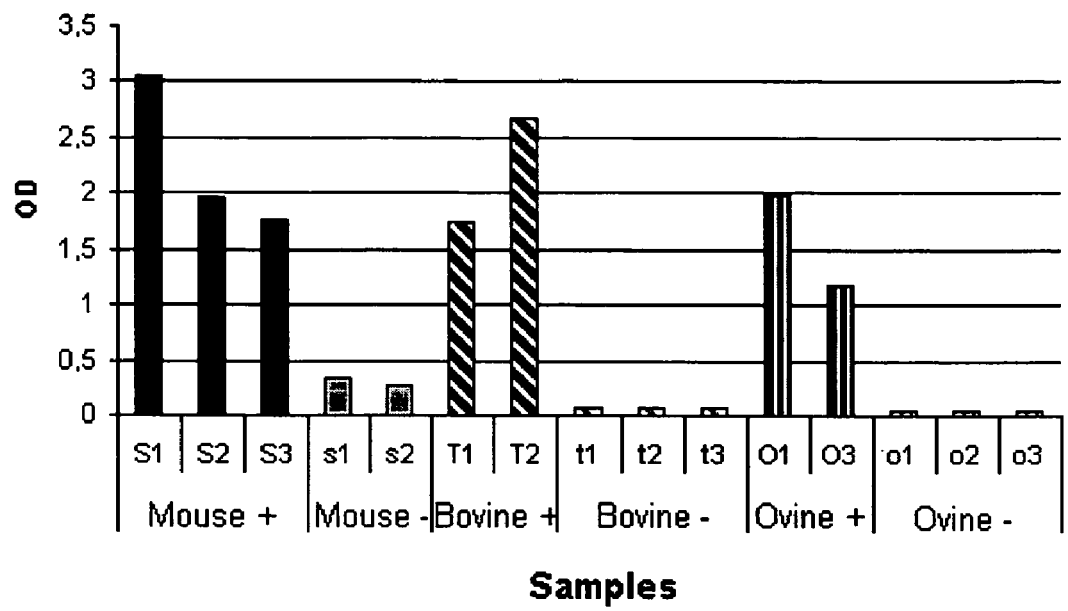

Wang et al., "Cytotoxicity of Poly(Phenolic)Sulfonates and Theior Sodium Salts in L1210 Lymphoid Leukemia Cells," Metal Based Drugs, vol. 5, No. 3, pp. 147-159, 1998.

Arduini et al., "Macrocycle Synthesis," Eds. Harwood, L.M. & Moddy, C.J. Oxford University Press, (1996).

* cited by examiner

METHOD FOR DETECTING PRP USING AT LEAST ONE POSITIVE CHARGE AND/OR AT LEAST ONE GLYCOSIDIC BOND AND A LIGAND OTHER THAN A PROTEIN LIGAND

The present invention relates to the field of prion diseases, and in particular to a method for detecting the forms of the prion associated with these diseases.

The native or normal prion protein, denoted $PrP^c$ for the cellular prion protein, is a glycoprotein that is widely expressed in mammalian lymphoid and neuronal cells.

Conformational changes in $PrP^c$ lead to the appearance and to the propagation of the pathological protein $PrP^{sc}$ which is resistant to proteinase K. This pathological protein will, in the present application, be called, without distinction, $PrP^{sc}$ or $PrP^{res}$. The term "PrP" will, in the present application, denote any form of PrP which may or may not be normal and which may or may not be resistant.

The accumulation of $PrP^{sc}$ in mammalian organs is the cause of numerous diseases, called prion diseases or transmissible spongiform encephalopathies (TSEs), and in particular scrapie in small ruminants, chronic wasting disease (CWD) in the elk and in the antelope, bovine spongiform encephalopathy (BSE), and Creutzfeldt-Jakob disease (CJD) in humans.

The development of the disease in the infected host is reflected by an accumulation of the pathological protein $PrP^{sc}$ in the brain, which leads to an irreversible impairment of the brain cells.

The late appearance, after an incubation period of 2 to 6 years, and the slow development of the symptoms in cattle infected with BSE has considerably slowed down the development of epidemiological models. BSE is transmissible to humans by ingestion and has led to the appearance of a new form of Creutzfeldt-Jakob disease (vCJD) in humans.

Detection of the pathological protein $PrP^{sc}$ is difficult in asymptomatic infected animals before the development of the disease, and especially in physiological fluids, such as blood and urine, in diseased animals. It is currently established that $PrP^{sc}$ present in animals intended for human food is transmitted to humans when infected tissues are ingested. A major public health objective is therefore to avoid this transmission by detecting the presence of $PrP^{sc}$:
  in animals intended for human consumption with the view to removing them from the food chain,
  in blood donations and blood derivatives intended for transfusion in humans. In fact, as shown by the presence of pathogenic protein $PrP^{sc}$ in the blood and the lymphoid cells well before the brain is affected, and therefore well before the possibility of detecting neurological signs evoking a clinically manifested prion disease, the physiopathology in humans is unknown. Since it is not possible to carry out experimental infections as in sheep, the absence of a test for detection in the blood or other biological fluids does not make it possible to study and therefore to prevent interhuman transmission via blood donation, or to envision a treatment of infected individuals before the beginning of brain lesions;
  in animal herds before the neurological stage, thus making it possible to eliminate the infected animals early, before they arrive at abattoirs.

The detection of the presence of $PrP^{sc}$ in biological samples in humans or in animals is therefore becoming extremely important, and several research teams are developing immunological detection methods (WO 02/086511). Moreover, methods for complexing, with $PrP^{sc}$, peptides, small molecules or inhibitors with a view to the treatment of vCJD are the subject of active research. However, the methods of the prior art constantly come up against the difficulty in identifying $PrP^{sc}$ reliably when it is in a small amount in a biological sample.

The present inventors have now demonstrated, against all expectations, that the use of a molecule having at least one positive charge and/or at least one glycosidic bond and of a ligand other than a protein ligand in a test for diagnosing PrP in a biological sample that may contain such a protein, makes it possible to detect this protein at dilutions and under conditions where it is not detectable with the methods currently used, the use of these two components in combination not modifying the ability of PrP to bind to a PrP-specific binding partner used in the diagnostic test.

Thus, a subject of the present invention is a method for detecting PrP, in particular $PrP^{sc}$, in a biological sample of human or animal origin that may contain PrP, characterized in that it uses a molecule having at least one positive charge and/or at least one glycosidic bond and a ligand other than a protein ligand.

It also relates to the diagnostic kits for detecting PrP, comprising a ligand other than a protein ligand and a molecule having at least one positive charge and/or at least one glycosidic bond.

The expression "ligand other than a protein ligand" is intended to mean a compound that is capable of binding to PrP and that is nonprotein in nature. By way of a protein ligand excluded from this ligand definition, mention may be made of anti-PrP antibodies.

The expression "molecule having at least one positive charge and/or at least one glycosidic bond" is intended to mean a molecule having at least one positive charge or a molecule having a function involved in a glycosidic bond, or else both.

The method of the invention therefore has the advantage of allowing the detection of PrP in biological samples where it is present in a small amount, by virtue of the combined use of a molecule having at least one positive charge and/or at least one glycosidic bond and of a ligand other than a protein ligand as defined above.

The biological samples in which the method of detection of the invention is carried out are any sample of animal or human origin that may contain PrP.

By way of example of such samples, mention may be made of the brain, central nervous system tissues, organs such as the spleen and the intestine, and also biological fluids such as cephalospinal fluid, urine and blood.

The animals to which the method of the invention may relate are is animals which develop prion diseases. By way of nonlimiting example, mention will be made of members of the ovine race and cattle.

By way of positive charge contained in the molecules having at least one positive charge and/or at least one glycosidic bond, positive charges provided by basic functions, such as guanidinium or ammonium functions, are preferred.

By way of glycosidic bond contained in the molecules having at least one positive charge and/or at least one glycosidic bond, bonds of heteroside type, such as those found in macrolides and aminoglycosides, are preferred.

The molecules having at least one positive charge and/or at least one glycosidic bond that are preferred for the purposes of the invention are molecules having both at least one positive charge and at least one glycosidic bond, and also molecules having at least two guanidinium and/or ammonium functions, preferably in a nonpolymeric hydrophilic molecular system.

According to a particular embodiment of the invention, the molecules having at least one positive charge and at least one glycosidic bond are chosen from aminoglycosides with a guanidinium ring, streptomycin being particularly preferred.

According to another particular embodiment of the invention, the molecules having at least two guanidinium and/or ammonium functions are chosen from polyallylamine, triethylenetetraamine (TET), bis-3-aminopropylamine, spermine tetrahydrochloride, dihydrostreptomycin sesquisulfate and streptomycin, the latter two compounds also belonging to the family of molecules having at least one positive charge and at least one glycosidic bond.

The use of a molecule having at least one positive charge and/or at least one glycosidic bond, in particular of a molecule having at least two guanidinium and/or ammonium functions, preferably streptomycin, more preferably in the form of a salt, allows the precipitation of the PrP present in the biological sample tested. This precipitation property is increased in the presence of $PrP^{sc}$, in particular after treatment with proteinase K ($PrP^{res}$). This precipitation is due to the formation of PrP aggregates (also called PrP crosslinked by the molecule having at least one positive charge and/or at least one glycosidic bond) obtained after treatment with the molecule having at least one positive charge and/or at least one glycosidic bond.

Thus, it is possible to detect PrP, in particular $PrP^{sc}$, by means of a method characterized in that a biological sample derived or obtained from an animal or human organism is brought into contact with a molecule having at least two guanidinium and/or ammonium functions, with the exception of the antibiotics corresponding to this definition, such as streptomycin.

This method can be implemented by means of the steps consisting in:

a) adding, to the biological sample derived or obtained from an animal or human organism, a molecule having at least two guanidinium and/or ammonium functions, with the exception of the antibiotics, b) subjecting the solution to heating (for example, between 37 and 150° C.), and then to centrifugation, and separating the pellet from the supernatant, c) detecting the $PrP^{sc}$ after migration on an electrophoresis gel, transfer and immunodetection, or after capture on a solid support followed by ELISA-type immunodetection.

The method can also comprise, as an additional step, a step consisting of denaturation under the conditions indicated hereinafter.

The method can also comprise, as an additional step, preferably preceding step a), a step consisting of addition of proteinase K under the conditions indicated hereinafter.

Similarly, the step for detecting $PrP^{sc}$ can be carried out under the conditions indicated hereinafter.

Because of their ability to bind to $PrP^{sc}$, the molecules having at least two guanidinium and/or ammonium functions, with the exception of the antibiotics, are particularly useful for the precipitation, the detection and/or the diagnosis of $PrP^{sc}$, even during detection by immunohistochemistry, and also for the elimination of $PrP^{sc}$ from a tissue or from a biological fluid.

The addition of a ligand other than a protein ligand, and in particular of a macrocyclic ligand or of a glycosaminoglycan, makes it possible, unlike protein ligands, to amplify the sensitivity of detection of the PrP protein and to more effectively capture the PrP crosslinked by the molecule having at least one positive charge and/or at least one glycosidic bond. As a result, PrP can be detected in biological samples where it is present only in small amounts.

The amount of molecule having at least one positive charge and/or at least one glycosidic bond, and also of the ligand other than a protein ligand, can be readily determined by those skilled in the art according to the specificities of the sample. Thus, for example, the amount of molecule having at least one positive charge and/or at least one glycosidic bond, such as streptomycin, can be between 50 and 500 mg/ml, preferably between 100 and 300 mg/ml.

Against all expectations, the action of a molecule having at least one positive charge and/or at least one glycosidic bond on PrP, and then the complexation of the ligand other than a protein ligand with the PrP aggregate thus formed, and vice-versa, does not in any way impair the detection of the PrP, for example using an anti-PrP detection antibody.

According to a particular embodiment of the invention, said molecule having at least one positive charge and/or at least one glycosidic bond is added to said biological sample so as to precipitate the PrP, before the addition of the ligand other than a protein ligand.

Preferably, in order to promote the precipitation of the PrP, after the addition of the molecule having at least one positive charge and/or at least one glycosidic bond, the reaction medium is moderately heated at a temperature of between 25 and 45° C., a temperature of 37° C. being preferred.

Before the biological sample to be tested is brought into contact with said molecule having at least one positive charge and/or at least one glycosidic bond, the sample can be pretreated with proteinase K so as to allow proteolytic digestion of the cellular PrP. The sample thus treated now contains, as prion protein, only the resistant $PrP^{sc}$ protein ($PrP^{res}$). The proteinase K treatment step is a discriminating step for determining prion diseases or contamination of the samples tested with $PrP^{sc}$, in the absence of an antibody or ligand specific for $PrP^{sc}$ or for $PrP^{res}$.

The amount of proteinase K to be used in the method of the invention can be readily determined by those skilled in the art. Thus, for example, it can be between 80 and 160 µg/ml.

Thus, according to a preferred embodiment, the method for detecting PrP of the invention comprises the additional step of adding proteinase K to the sample. This proteinase K digestion step can be carried out either before crosslinking of the PrP with said molecule having at least one positive charge and/or at least one glycosidic bond, or after such a crosslinking.

According to yet another embodiment, the method of the invention comprises the steps consisting in:

a) adding proteinase K to said sample so as to digest the $PrP^c$, b) adding, to the mixture thus obtained, said molecule having at least one positive charge and/or at least one glycosidic bond so as to obtain PrP aggregates, c) adding a ligand other than a protein ligand, and d) revealing the presence of $PrP^{res}$.

The PrP aggregates formed in the presence of the molecule having at least one positive charge and/or at least one glycosidic bond and containing PrP can be separated from the reaction medium before their reaction with the ligand other than a protein ligand, whether or not there is pretreatment with proteinase K. The separation method is carried out by any method for separating a precipitate known to those skilled in the art. By way of example, the PrP aggregates are separated from the reaction medium by centrifugation, and then by removal of the supernatant. This separation step makes it possible to eliminate all products that are not required for the subsequent reaction for detecting PrP, such as the proteinase K, where appropriate, the digested proteins and the molecule having at least one positive charge and/or at least one glycosidic bond free in solution.

In order to further improve the sensitivity of the method of detection of the invention, before the reaction of the PrP aggregates with the ligand other than a protein ligand, it is also possible to carry out a denaturation of said aggregates present in the biological sample to be tested. This denaturation step can be carried out by any method for denaturating protein aggregates known to those skilled in the art. Preferably, the denaturation is carried out by adding guanidine HCl.

Thus, the method for detecting PrP according to the invention preferably comprises at least one of the following additional steps i) and ii), consisting in:
i) separating the PrP aggregates from the reaction mixture, and
ii) denaturing the PrP aggregates,
these steps being included, where appropriate, between step b) and step c).

According to a preferred embodiment, the method of detection of the invention implements the two steps i) and ii) successively, preferably between step b) and step c).

The revelation of the presence of PrP in a biological sample according to the method of the invention can be carried out according to the conventional methods for detecting analytes in a sample.

It can, for example, be carried out by immunodetection or non-immunodetection.

The term "immunodetection" is intended to mean the demonstration of an immunoreaction with PrP, this immunoreaction consisting of binding between the PrP to be detected and a PrP-specific binding partner, or else of a competition reaction between the PrP that may be contained in the sample to be tested and the labeled PrP.

By way of nonimmunodetection, mention may, for example, be made of electrophoresis gel staining techniques well known to those skilled in the art.

The detection of PrP by immunoreaction can be carried out, for example, after addition of a PrP-specific binding partner.

The term "PrP-specific binding partner" is intended to mean any partner capable of binding to PrP. The visualization of the immunoreaction will then consist of the visualization of the PrP-specific binding partner/PrP complex.

According to a preferred embodiment, the method of the invention is such that a PrP-specific binding partner for the immunoreaction between the PrP-specific binding partner and the PrP is added, where appropriate, in step d).

By way of PrP-specific binding partner, mention may, for example, be made of antibodies, antibody fragments, polypeptides, proteins, nucleic acids, haptens and aptamers.

The term "antibodies" includes polyclonal or monoclonal antibodies, antibodies obtained by genetic recombinations and antibody fragments.

The polyclonal antibodies can be obtained by immunization of an animal with at least one target antigen of interest, in the present case PrP, followed by recovery of the desired antibodies in purified form, by sampling the serum of said animal, and separating said antibodies from the other serum constituents, in particular by affinity chromatography on a column to which is attached an antigen specifically recognized by the antibodies, in particular the PrP.

The monoclonal antibodies can be obtained by the hybridoma technique, the general principle of which is recalled hereinafter.

Firstly, an animal, generally a mouse (or cells in culture in the case of in vitro immunizations) is immunized with a target antigen of interest, in the present case PrP, the B lymphocytes of which are then capable of producing antibodies against said antigen. These antibody-producing lymphocytes are then fused with "immortal" myeloma cells (murine cells in the example) so as to give rise to hybridomas. Using the heterogeneous mixture of cells thus obtained, a selection of cells capable of producing a specific antibody and of multiplying indefinitely is then carried out. Each hybridoma is multiplied in the form of a clone, each resulting in the production of a monoclonal antibody whose recognition properties with respect to the antigen of interest may be tested, for example, by ELISA, by one- or two-dimensional immuno blotting, by immunofluorescence, or using a biosensor. The monoclonal antibodies thus selected are subsequently purified, in particular according to the affinity chromatography technique described above.

By way of appropriate antibodies for the invention, mention may, for example, be made of the antibodies 8G8, 12F10 (SpiBio, France) and 3F4 (Immunok).

The antibody fragments are such that they conserve the PrP-binding function.

The term "polypeptide" is intended to mean a chain of at least two amino acids. The term "amino acids" is intended to mean the primary amino acids which encode proteins, the amino acids derived after enzymatic action, such as trans-4-hydroxyproline, and amino acids which are natural but not present in proteins, such as normalized, N-methyl-L-leucine or staline (Hunt S. in Chemistry and Biochemistry of the amino acids, Barett G C, ed., Chapman and Hall, London, 1985), amino acids protected with chemical functions that can be used in solid-support or liquid-phase synthesis, and unnatural amino acids.

The term "protein" includes holoproteins and heteroproteins such as nucleoproteins, lipoproteins, phosphoproteins, metalloproteins and glycoproteins, both fibrous and globular.

The term "nucleic acid" is intended to mean oligonucleotides, deoxyribonucleic acids and ribonucleic acids, and derivatives thereof.

The term "oligonucleotide" denotes a chain of at least 2 nucleotides (deoxyribonucleotides or ribonucleotides, or both), which may be natural or modified. The term "modified nucleotide" is intended to mean, for example, a nucleotide comprising a modified base and/or comprising a modification at the level of the internucleotide bond and/or at the level of the backbone. By way of example of a modified base, mention may be made of inosine, methyl-5-deoxycytidine, dimethylamino-5-deoxyuridine, diamino-2,6-purine and bromo-5-deoxyuridine. To illustrate a modified internucleotide bond, mention may be made of phosphorothioate, N-alkylphosphoramidate, alkylphosphonate and alkylphosphodiester bonds. Alpha-oligonucleotides such as those described in FR-A-2 607 507, LNAs such as phosphorothioate-LNA and 2'-thio-LNA described in Bioorganic & Medicinal Chemistry Letters, Volume 8, Issue 16, 18 Aug. 1998, pages 2219-2222, and the PNAs which are the subject of the article by M. Egholm et al., J. Am. Chem. Soc. (1992), 114, 1895-1897, are examples of oligonucleotides consisting of nucleotides whose backbone is modified.

The term "hapten" denotes nonimmunogenic compounds, i.e. compounds incapable, by themselves, of promoting an immune reaction by antibody production, but capable of being recognized by antibodies obtained by immunization of animals under known conditions, in particular by immunization with a hapten-protein conjugate. These compounds generally have a molecular mass of less than 3000 Da, and most commonly less than 2000 Da, and may, for example, be glycosylated peptides, metabolites, vitamins, hormones, prostaglandins, toxins or various medicinal products, nucleosides and nucleotides.

Aptamers are capture partners which are protein and nucleic in nature, and the function of which is to act as an antibody and to bind to protein ligands (Toulmé, J. J. and Giege, R., 1998, Medicine Science, 14(2), 155-166).

These polypeptides, proteins, haptens and aptamers all have the ability to bind to PrP or to the PrP aggregate.

The visualization of the immunoreaction between the PrP-specific binding partner and PrP that is carried out, in particular in step d), can be performed by any means of detection known to those skilled in the art, such as direct or indirect means.

In the case of direct detection, i.e. without the involvement of labeling, the immunoreaction is, for example, observed by plasmon resonance or by cyclic voltametry on an electrode bearing a conductive polymer.

In the case of indirect detection, i.e. involving labeling, the labeling can be carried out by means of said PrP-specific binding partner, which will then be labeled beforehand.

The visualization of the presence of PrP in a biological sample according to the method of the invention can also be carried out according to a "competition" method. PrP labeled beforehand is then added, in particular in step d), in place of the PrP-specific binding partner. In this case, the detection signal is at a maximum in the absence of PrP, and then gradually decreases as the concentration of PrP being sought, which is not labeled, increases due to the competition reaction.

The term "labeling" is intended to mean the attachment of a label capable of directly or indirectly generating a detectable signal. A nonlimiting list of these labels consists of:

- enzymes which produce a signal that is detectable, for example, by colorimetry, fluorescence or luminescence, such as horseradish peroxidase, alkaline phosphatase, α-galactosidase or glucose-6-phosphate dehydrogenase,
- chromophores such as luminescent compounds or dyes, radioactive molecules such as $^{32}P$, $^{35}S$ or $^{125}I$,
- fluorescent molecules such as fluorescein, rhodamine, alexa or phycocyanins, and
- particles such as gold particles, magnetic latex particles or liposomes.

Indirect systems can also be used, for instance by means of another ligand/antiligand pair. The ligand/antiligand pairs are well known to those skilled in the art, and mention may, for example, be made of the following pairs: biotin/streptavidin, hapten/antibody, antigen/antibody, peptide/antibody, sugar/lectin, polynucleotide/polynucleotide complementary thereto. In this case, it is the ligand which carries the binding agent. The antiligand can be detectable directly by means of the labels described in the previous paragraph, or can itself be detectable by means of a ligand/antiligand.

These indirect detection systems can, under certain conditions, result in an amplification of the signal. This signal amplification technique is well known to those skilled in the art, and reference may be made to the article J. Histochem. Cytochem. 45: 481-491, 1997.

Protein labeling is widely known to those skilled in the art and is described, for example, by Greg T. Hermanson in Bioconjugate Techniques, 1996, Academic Press Inc, 525B Street, San Diego, Calif. 92101 USA.

According to the type of labeling used, for instance using an enzyme, those skilled in the art will add reagents for visualizing the labeling.

Such reagents are widely known to those skilled in the art and are described in particular in Principles and Practice of Immunoassay, $2^{nd}$ Edition, Edited by C. Price, D. J. Newman Stockton Press, 1997, 345 Park Avenue South, New York.

The PrP detection can be a solid-phase detection, i.e. using a solid phase on which is immobilized a binding partner intended to capture the protein to be detected. In the case of the present invention, it is the ligand other than a protein ligand which serves as capture partner pre-immobilized on a solid support. An example of solid-phase detection well known to those skilled in the art is sandwich-type detection, such as ELISA-type detection.

Thus, according to a preferred embodiment of the invention, the ligand other than a protein ligand is bound to a solid support.

By way of solid support, mention may, for example, be made of beads, such as magnetic beads, and mitrotitration plates.

The ligand other than a protein ligand can be bound to the solid support in a manner known to those skilled in the art, such as by adsorption or covalent bonding, covalent bonding being preferred.

Thus, the solid support can be functionalized with a function capable of forming a bond with a function carried by the ligand. According to a preferred embodiment, the solid support is functionalized with an NHS (N-hydroxysuccinimide) bond or with an $NH_2$ function. This function can react with a function carried by the ligand. In this embodiment, the ligands carrying a function capable of reacting so as to form a bond with the functional bond of the solid support, in particular carrying an $NH_2$ or COOH bond, are particularly preferred.

Examples of ligands other than protein ligands include, for example, macrocyclic ligands and glycosaminoglycans.

These ligands all have the particularity, unlike protein ligands, of amplifying the PrP protein detection sensitivity.

According to one embodiment of the invention, the ligand other than a protein ligand is chosen from macrocyclic ligands and glycosaminoglycans.

Glycosaminoglycans are widely known to those skilled in the art and are described, for example, in Polysaccharides, M. Yalpani, Elsevier, Amsterdam, 1988.

By way of glycosaminoglycans appropriate for the purposes of the invention, mention may, for example, be made of heparin, chondroitin sulfate, dermatan sulfate, hyaluronic acid and keratin sulfate.

The term "macrocyclic ligand" is intended to mean a compound consisting of a succession of rings forming a macrocycle.

The macrocyclic ligands are well known to those skilled in the art. By way of nonlimiting examples, mention may be made of cyclophanes, metacyclophanes, cyclodextrins, cyclo (tetra-chromotropic acid)s, spherands and cyclo[n]veratrylenes.

The macrocyclic ligands have the particular advantage that they make it possible to trap the protein to be tested in free form or in the form of an aggregate, via a cage effect.

The macrocyclic ligands can be prepared according to the techniques known to those skilled in the art, for example described in Comprehensive Supramolecular Chemistry, Pergamon, Oxford, 1996.

The macrocyclic ligands that are preferred for the method of the invention are chosen from metacyclophanes, calixarenes being particularly preferred. Such calixarene compounds can be obtained according to the methodology described in Arduini, A. et al., 1996, Macrocycle Synthesis, Eds. Harwood, L. M. & Moddy, C. J. Oxford University Press, Oxford and Da Silva et al., 2001, J. Supramol. Chem., 1:135-138.

According to a preferred embodiment, the macrocyclic ligand of the invention corresponds to general formula (I) below:

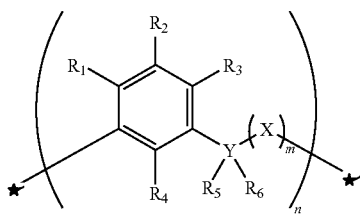

(I)

in which $R_1$ represents a hydrogen atom, a hydroxyl group, an OR group or an OCOR group, R being as defined below, $R_2$ represents a hydrogen atom or an R, COR, Pol or $CH_2Pol$ group, in which Pol represents a phosphate, sulfate, amine, ammonium or carboxylic acid group, and R is as defined below, $R_3$ represents a hydrogen atom, a hydroxyl group, an OR group or an OCOR group in which R is as defined below, $R_4$ represents a hydrogen atom, a hydroxyl group, an OR group, an $OCH_2R$ group or an OCOR group, in which R is as defined below, Y is a carbon, nitrogen or sulfur atom, $R_5$ and $R_6$, each independently, are absent or represent a hydrogen atom, a $CH_2$ group or an R group as defined below, or else $R_5$ and $R_6$ together represent an oxygen or sulfur atom, X represents a $CH_2$ group, or an oxygen or sulfur atom, m represents an integer equal to 0 or 1, R represents a hydrogen atom or a saturated or unsaturated, branched or unbranched, cyclic or noncyclic hydrocarbon-based chain which may or may not be substituted with a halogen group, and which carries polar or nonpolar functions, n is an integer between 3 and 15, the substituents $R_1$ to $R_5$, R, X and Y and the integer m may be different in nature according to the units.

Thus, the compound of formula (I) is in the form of a succession of n units characterized by the presence of a benzene ring, and the substituents of this ring can be variable from one unit to the other, within the limit of their definitions above.

The saturated or unsaturated, branched or unbranched, cyclic or noncyclic hydrocarbon-based chains which may or may not be substituted with a halogen group, and which carry polar or nonpolar functions, are widely known to those skilled in the art. By way of examples, mention may be made of alkyls, alkenes, aryls and saturated rings such as cyclohexane. An example of a nonpolar group is $CF_3$ and examples of polar groups are the substituents Pol as defined above.

The compounds of formula (I) that are particularly preferred correspond to formula (Ia) below:

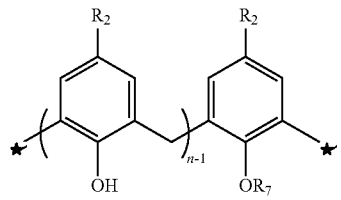

(Ia)

in which n is an integer between 4 and 8, each group $R_2$, taken independently, is a sulfate group or a phosphate group, $R_7$ represents a $(CH_2)_t$—$(CO)_s$—$(NH_2)$ group or a $(CH_2)_t$—COOH group where t is an integer between 0 and 6 and s is an integer between 0 and 6.

The compounds of formula (Ia) that are particularly preferred are those for which the two groups $R_2$ are each a sulfate group, n is 4, 6 or 8, and $R_7$ is a hydrogen atom, a —$CH_2COOH$ group, a —$CH_2CONH_2$ group or a —$CH_2CH_2NH_2$ group, which constitutes an embodiment of the invention.

According to a preferred embodiment, the macrocyclic ligand corresponds to general formula (Ia) in which n=6, each $R_2$=sulfate and $R_7$ is —$CH_2CH_2NH_2$.

For the implementation of the method for immunodetecting pathogenic PrP of the invention, use may be made of diagnostic kits comprising a ligand other than a protein ligand, preferably a macrocyclic ligand, and a molecule having at least one positive charge and/or at least one glycosidic bond.

According to a preferred embodiment, said ligand other than a protein ligand present in the kit is bound to a solid support for carrying out the detection of pathogenic PrP according to a solid-phase detection method.

Figure 2:
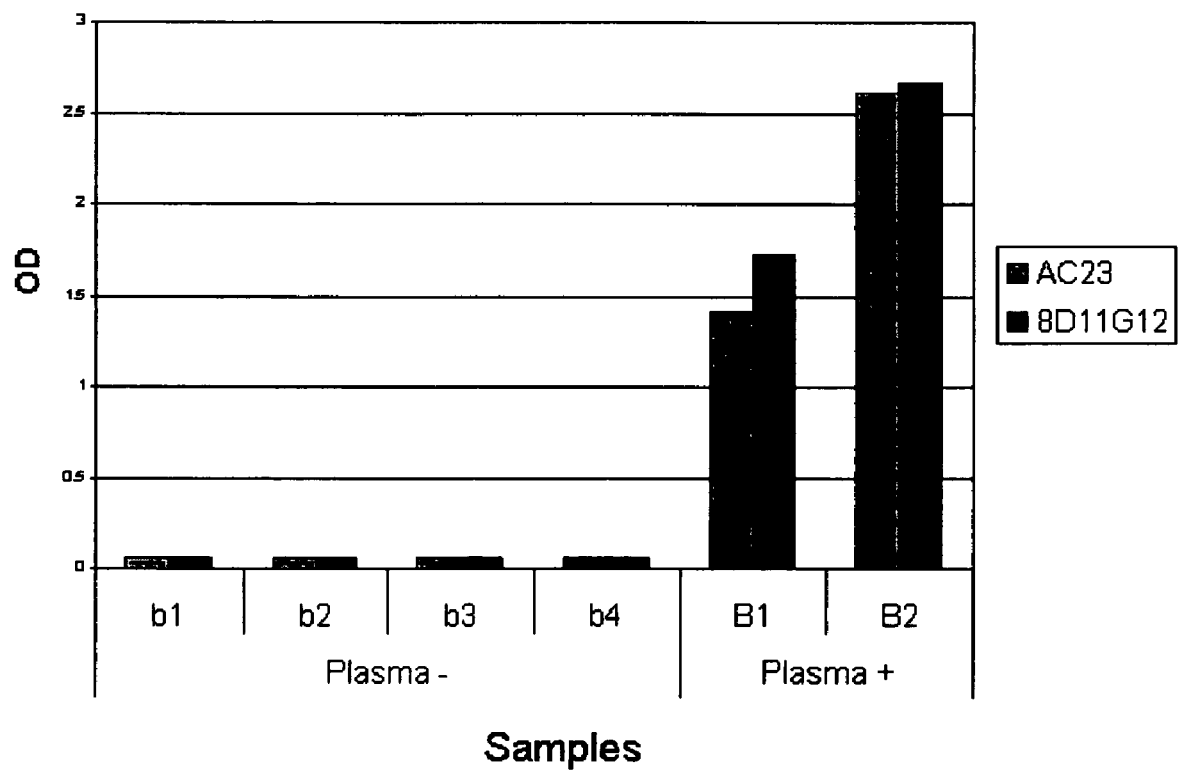
Figure 3:
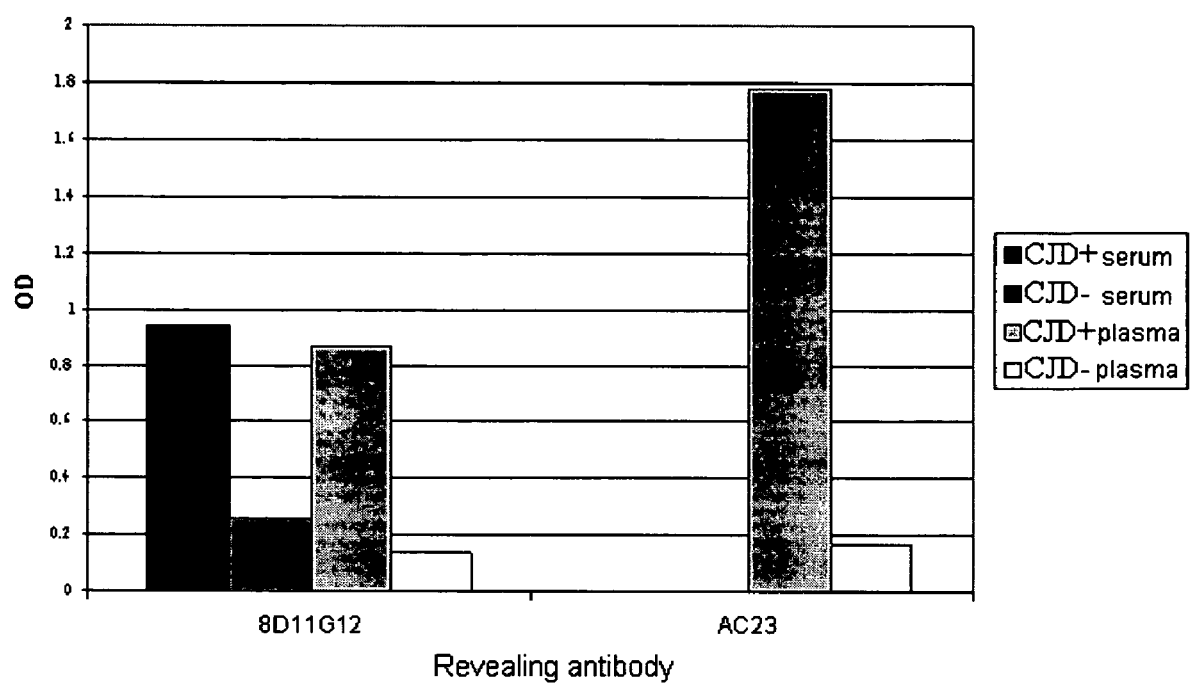
Figure 4A:
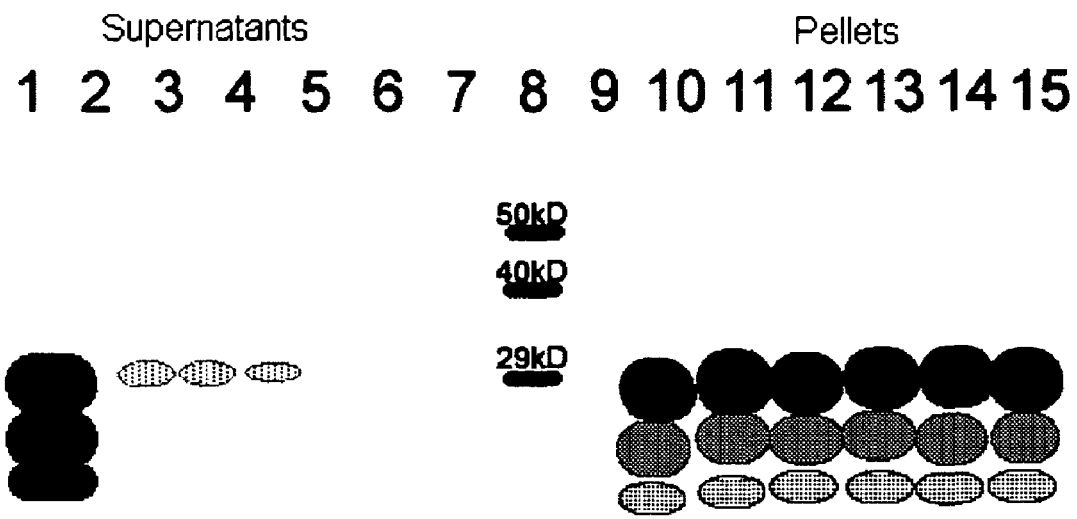
Figure 4B:
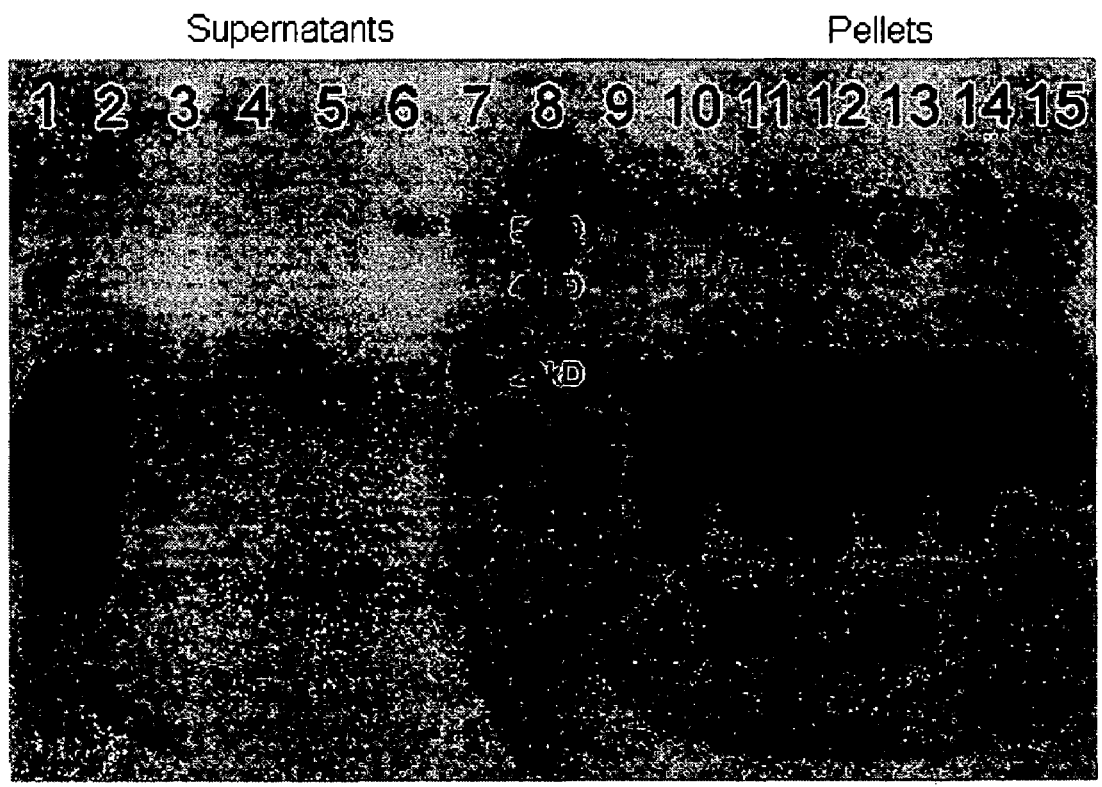
Figure 5A:
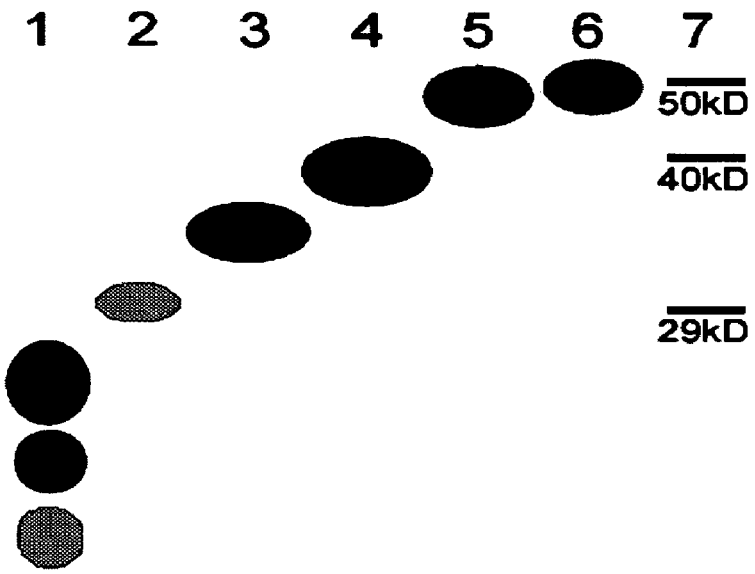
Figure 5B:
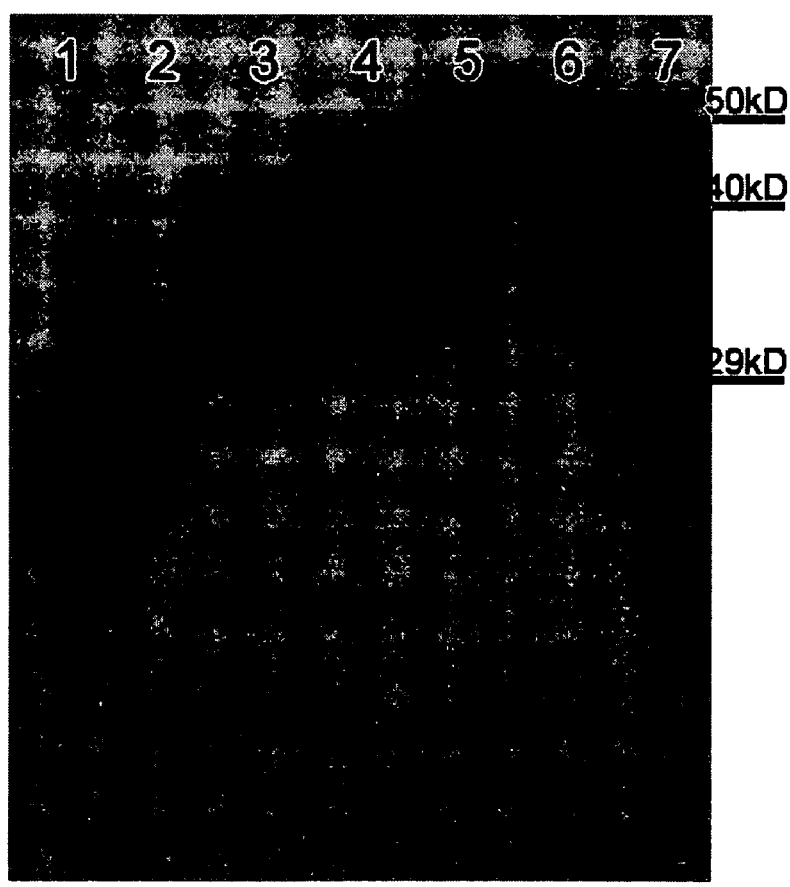
Figure 6A:
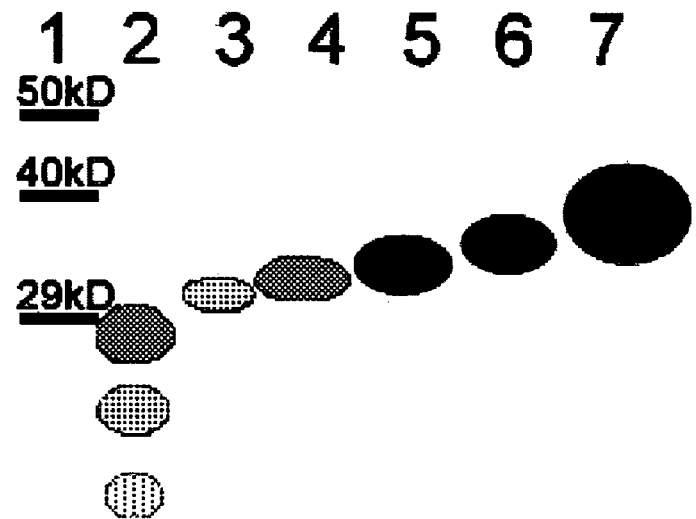
Figure 6B:
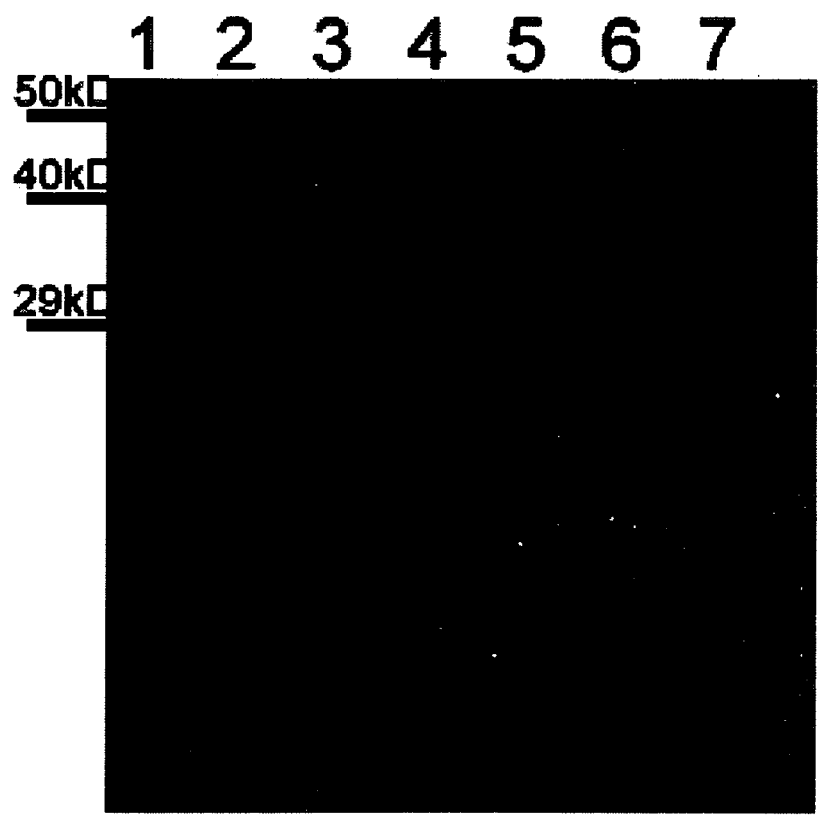
Figure 7A:
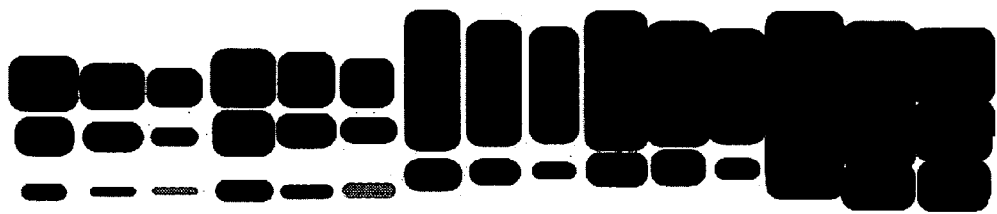
Figure 7B:
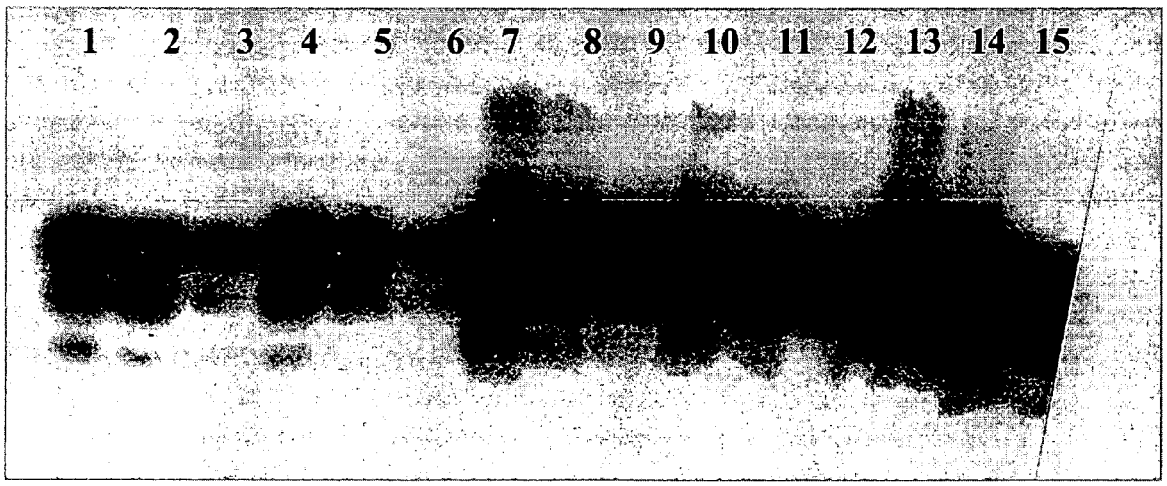
Figure 8A:
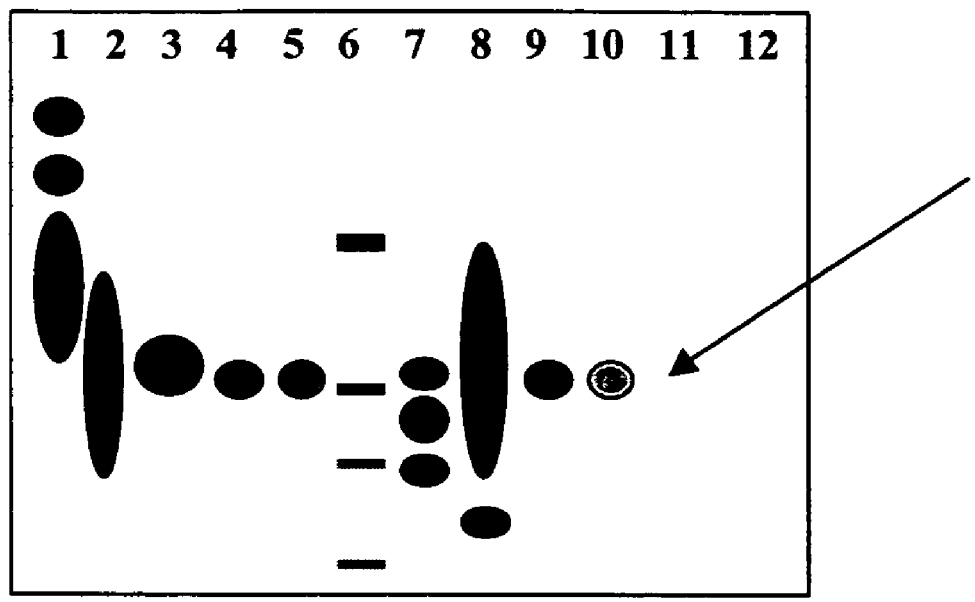
Figure 8B:
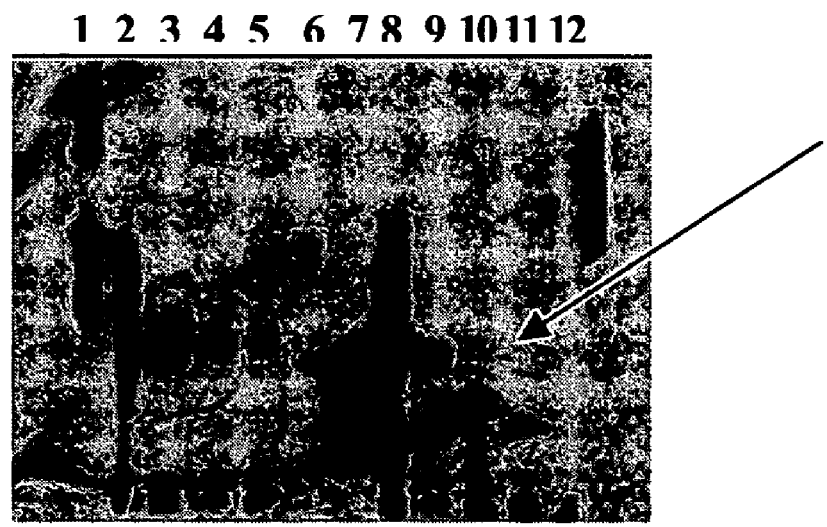
Figure 9A:
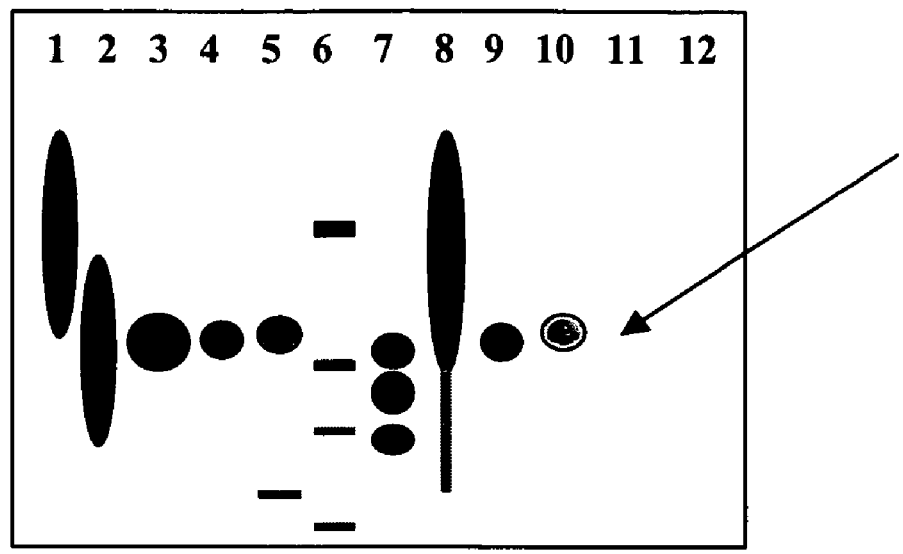
Figure 9B:
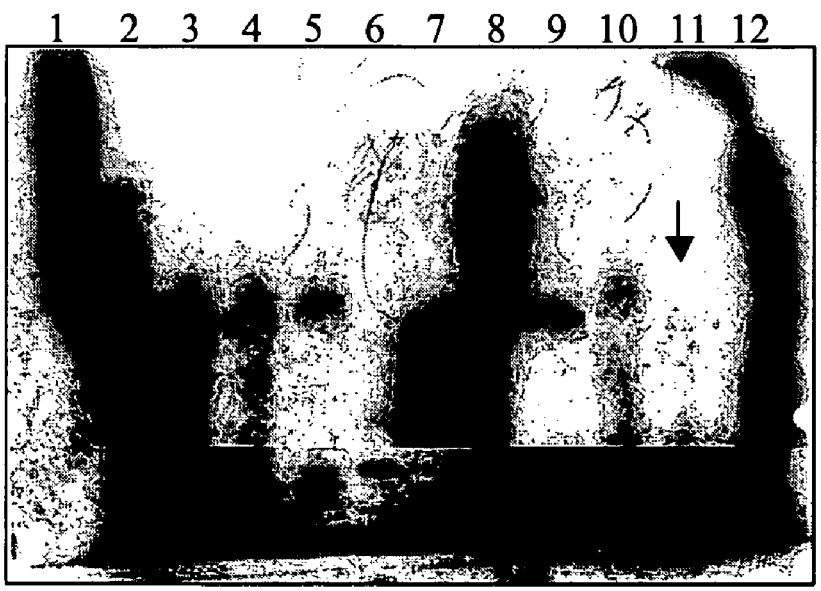
Figure 10A:
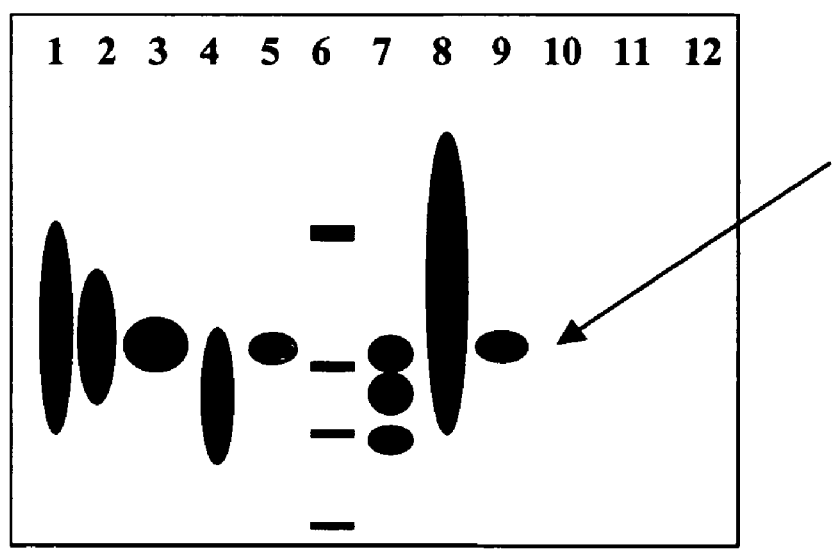
Figure 10B:
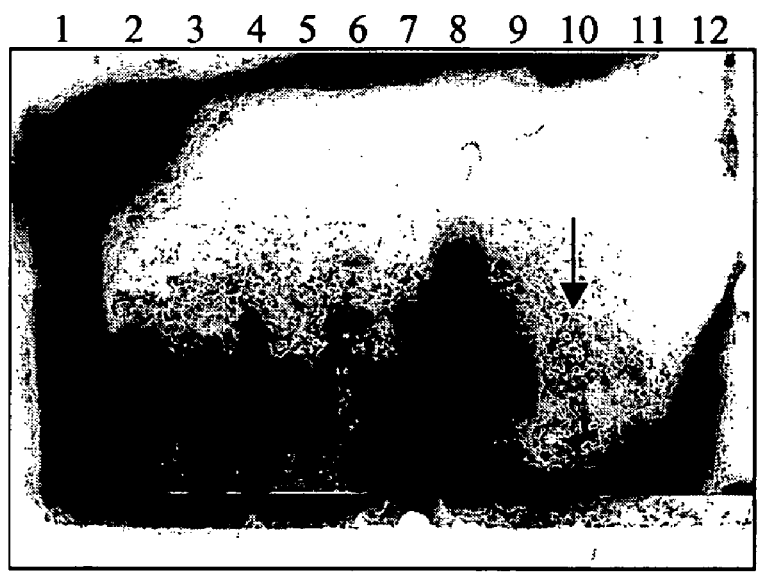

The invention will be understood more fully from the following examples given by way of nonlimiting illustration, and also from FIGS. 1 to 10, in which:

FIG. 1 is a graphic representation giving the OD values obtained after detection, by the method of the invention, of $PrP^{res}$ in samples of mouse serum, of ovine sera and of bovine plasmas, which are positive (+) or negative (−), FIG. 2 is a graphic representation giving the OD values obtained after detection, by the method of the invention, of $PrP^{res}$ in samples of positive (plasma +) or negative (plasma −) bovine plasmas using two different revealing antibodies, FIG. 3 is a graphic representation giving the OD values obtained after detection, by the method of the invention, of $PrP^{res}$ in samples of human sera and human plasmas positive with respect to Creutzfeldt-Jakob disease (CJD +) or negative (CJD −) using two different revealing antibodies, FIG. 4 is a diagrammatic representation (FIG. 4A) of an electrophoresis gel (FIG. 4B) following Western blotting, obtained after migration of BSE bovine brain samples treated either with streptomycin sesquisulfate (lanes 5-7 and 13-15), or with streptomycin (lanes 2-4 and 10-12), lanes 1 and 9 corresponding to the nontreated control and lane 8 corresponding to the molecular weight marker lane, FIG. 5 is a diagrammatic representation (FIG. 5A) of an electrophoresis gel (FIG. 5B) following Western blotting, obtained after migration of BSE bovine brain samples treated with increasing amounts of triethylenetetramine (lanes 2-6), lane 1 corresponding to the nontreated control and lane 8 corresponding to the molecular weight marker lane, FIG. 6 is a diagrammatic representation (FIG. 6A) of an electrophoresis gel (FIG. 6B) following Western blotting, obtained after migration of BSE bovine brain samples treated with increasing amounts of bis-3-aminopropylamine (lanes 3-7), lane 2 corresponding to the nontreated control and lane 1 corresponding to the molecular weight marker lane, FIG. 7 is a diagrammatic representation (FIG. 7A) of an electrophoresis gel (FIG. 7B) following Western blotting, obtained after migration of BSE bovine brain samples treated with streptomycin and the calixarene p-sulfonato-3,7-(2-aminoethyloxy)calix-[6]-arene (lanes 7 to 15), lanes 1 to 3 corresponding to the control samples without the addition of streptomycin or calixarene, and lanes 4 to 6 corresponding to the samples in which only the calixarene was added, FIG. 8 is a diagrammatic representation (FIG. 8A) of an electrophoresis gel (FIG. 8B) following Western blotting, obtained after migration of samples of normal human blood (or negative for Creutzfeldt-Jakob disease) overloaded with 1% of spleen homogenate, positive or negative for Creutzfeldt-Jakob disease (respectively CJD+ or CJD−), treated with streptomycin and heparin (lanes 1 to 5 for CJD+ and lanes 8 to 12 for CJD−), lane 6 corresponding to the molecular weight marker lane and lane 7 corresponding to the positive control sample, FIG. 9 is a diagrammatic representation (FIG. 9A) of an electrophoresis gel (FIG. 9B) following Western blotting, obtained after migration of samples of normal human blood overloaded with 5% of spleen homogenate, positive or negative for Creutzfeldt-Jakob disease (respectively CJD+ or CJD−), treated with streptomycin and heparin (lanes 1 to 5 for CJD+ and lanes 8 to 12 for CJD−), lane 6 corresponding to the molecular weight marker lane and lane 7 corresponding to the positive control sample, and FIG. 10 is a diagrammatic representation (FIG. 10A) of an electrophoresis gel (FIG. 10B) following Western blotting, obtained after migration of samples of normal human blood overloaded with 10% of spleen homogenate, positive or negative for Creutzfeldt-Jakob disease (respectively CJD+ or CJD−), treated with streptomycin and heparin (lanes 1 to 5 for CJD+ and lanes 8 to 12 for CJD−), lane 6 corresponding to the molecular weight marker lane and lane 7 corresponding to the positive control sample.

EXAMPLE 1

Pretreatment of the Samples

1. Samples of Solid Organs Such as Brain Extract, Not Treated with Streptomycin

The organs (brain, etc.) are first of all homogenized in a 5% (w/v) glucose solution in order to obtain a 10% suspension.

5 µl of a 2 mg/l solution of proteinase K (PK), 1 µl of a 10% SDS (sodium dodecyl sulfate) solution and 6 µl of a 2.5% w/v solution of N-octyl-$\beta$-$_D$-glycopyranoside in water are added to 100 µl of the homogenized solution described above.

The mixture is vortexed and then incubated at 37° C. for 60 minutes.

500 µl of a chloroform:methanol (1:2) mixture are then added and the mixture is subjected to vortexing.

This is followed by a centrifugation step at 15 000 rpm at room temperature for 10 minutes.

The supernatant is then removed and the pellet is resuspended in 25 µl of a 6M guanidine hydrochloride solution. The suspension is incubated at 37° C. for 30 minutes.

Finally, 400 µl of a solution of PBS (phosphate buffered saline) and Tween 20 (0.05% w/v) are added.

2. Samples of Solid Organs Such as Brain Extract, Treated with Streptomycin

The organs (brain, spleen, etc.) are first of all homogenized in a 5% (w/v) glucose solution in order to obtain a 10% suspension.

5 µl of a 2 mg/l solution of proteinase K (PK) and 20 µl of a 2.5% w/v solution of N-octyl-$\beta$-$_D$-glycopyranoside in water are added to 100 µl of the homogenized solution described above. The mixture is vortexed and then incubated at 37° C. for 30 minutes.

20 µl of a solution of streptomycin sulfate at a concentration of 1 g/ml are added, and the mixture is stirred and reincubated at 37° C. for 1 hour.

500 µl of a chloroform:methanol (1:2) mixture are then added and the mixture is subjected to vortexing.

This is followed by a centrifugation step at 10 000 rpm at room temperature for 10 minutes.

The supernatant is then removed and the pellet is resuspended in 25 µl of a 6M guanidine hydrochloride solution. The suspension is incubated at 37° C. for 30 minutes.

Finally, 400 µl of a solution of PBS and Tween 20 (0.05% w/v) are added.

3. Samples of Biological Fluids Such as Serum and Plasma, Treated with Streptomycin A proteinase K solution is added to 100 µl of serum or plasma such that the final concentration of enzyme is 80 µg/ml. The solution is then mixed by vortexing and incubated at 37° C. for 30 minutes.

20 µl of a streptomycin sulfate solution at a concentration of 1 g/ml are added, and the mixture is stirred and reincubated at 37° C. for 1 hour.

After centrifugation at 15 000 rpm for 10 minutes, the supernatant is discarded.

The residual pellet is resuspended in 25 µl of a 6M solution of guanidine hydrochloride in water by means of vortexing. The suspension is then incubated at 37° C. for 30 minutes.

400 µl of a solution of PBS with 0.05% (w/v) of Tween 20 buffer are then added, and the mixture is vortexed.

4. Sample of Purified Digested (PrP$^{res}$) PrP$^{sc}$ Fibrils (SAF), Prepared from the Nervous System The organs (brain, etc.) are first of all homogenized in a 5% (w/v) glucose solution in order to obtain a 10% suspension, and filtered.

The PK is used in a proportion of 25 µg per 100 mg of tissue. After homogenization with the vortex, the tube is placed in an incubator at 37° C. for 1 hour.

The action of the PK is stopped by homogenization with Pefabloc® at 10 mM.

The preparation for the ultracentrifugation comprises homogenization of 1000 µl of digested ground material with 600 µl of 30% Sarkosyl. The mixture is left at room temperature for at least 15 minutes before being transferred onto a sucrose cushion (400 µl of 10% sucrose) in ultracentrifugation tubes (Beckman, Quick Seal, 2.2 ml). The tube is filled up with ultrapure water, and then heat-sealed and placed in the ultracentrifugation rotor.

This ultracentrifugation lasts 2 hours at 100 000 rpm and 20° C.

⅔ of the supernatant, including the lipid fraction, are then suctioned off. The pellet is dried by turning upside down onto absorbent paper.

The pellet is then taken up with 100 or 200 µl of PBS for immediate use or of denaturation buffer for freezing. In the latter case, the pellets are heated at 100° C. for 10 minutes.

After cooling, the tubes are centrifuged for 5 minutes at 12 000 rpm at 20° C. The supernatants are frozen at −80° C.

These samples serve as "positive" purified PrP$^{res}$ standards.

EXAMPLE 2

Preparation of the Calixarene Ligand p-sulfonato-3, 7-(2-amino-ethyloxy)calix-[6]-arene (Called C6S)

1. Preparation

This C6S macrocyclic adjuvant ligand has the general formula:

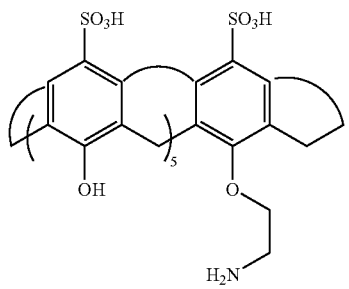

This ligand is prepared according to the method described in Eric Da Silva and Anthony W. Coleman, Synthesis and complexation properties towards amino acids of mono-substituted p-sulphonato-calix-[n]-arene, Tetrahedron 59 (2003) 7357-7364.

This ligand can then be coupled to a solid support (bead or plate) bearing an activated surface as indicated hereinafter.

2. Grafting of the C6S Ligand Onto Plates

The 96-well "NHS activated plates" are from the company Covalab (Lyon, France). 100 μl of a ligand solution are dissolved at various concentrations in 50 mM phosphate buffer, pH 8.2. The wells are washed 3 times (3×200 μl) with MilliQ water after incubation for two hours at 37° C. The plates are dried at room temperature before they are used.

Grafting Scheme:

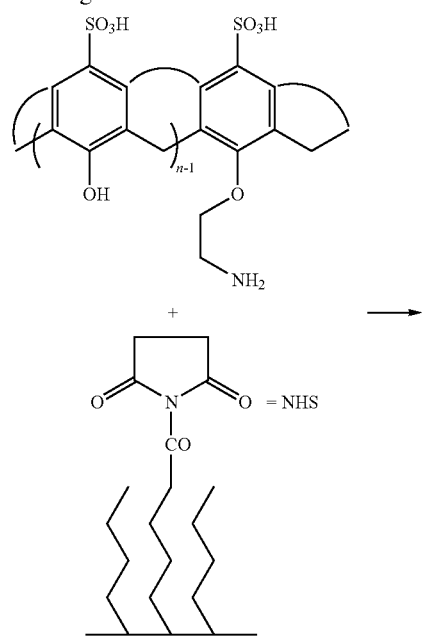

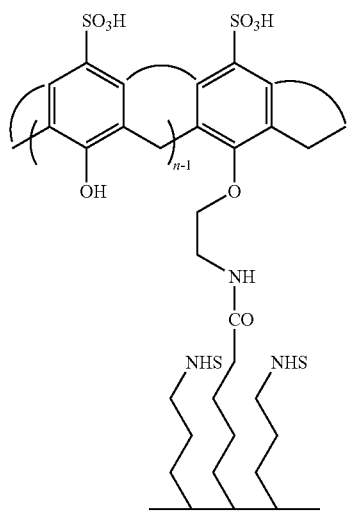

3. Grafting Onto Beads:

4 ml of an NHS activated bead solution (2×10$^9$ beads/ml; Dynabeads® M270Amine, company Dynals, Norway) are aliquoted into 1 ml tubes. The beads are centrifuged and precipitated by magnetization. The supernatant is removed and the beads are washed 3 times with 1 ml of water. The bead pellet is taken up with various volumes of calixarene solution in a 50 mM phosphate buffer, pH 8.2. 600 μl, 120 μl, 60 μl and 12 μl of a ligand solution at 50 mg/ml (50 mM phosphate buffer, pH 8.2) are added. The beads are stirred at room temperature for 24 hours. The beads are washed 3 times with MilliQ 18Ω water in order to remove the ligand which has not reacted. The beads are conserved in 1 ml of water in order to reconstitute the initial concentration of 2×10$^9$ beads/ml. The bead solution is ready to use. These beads are defined as "C6S beads" throughout the text.

Scheme for Grafting of C6S Onto the Beads:

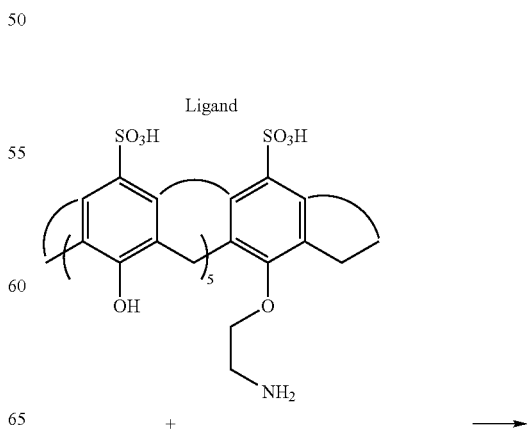

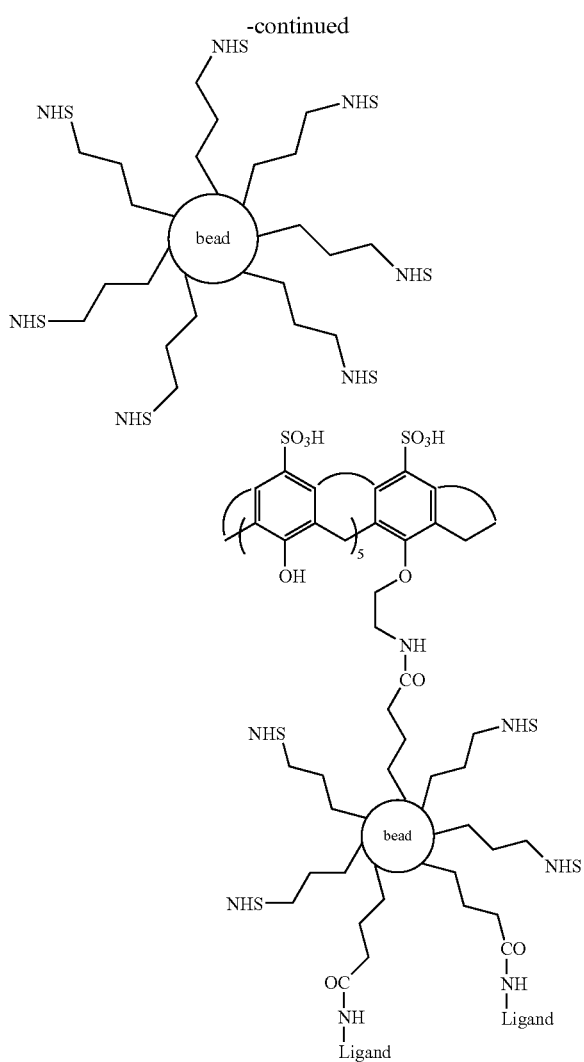

EXAMPLE 3

Detection of PrP$^{res}$

1. Samples Used

The positive bovine brain, serum and plasma samples are derived from animals which have been confirmed to be suffering from a TSE (transmissible spongiform encephalitis) prion disease by conventional reference methods, including a search, by Western blotting, for PrP$^{res}$ in the brain tissue, as described by Madec et al, 2000, Microbiol pathogenesis, 28: 353-362. The negative controls correspond to samples of brains, serum and plasma from animals for which the possibility of them suffering from prion diseases has been ruled out by the same analyses. The anticoagulant used for the plasma samples is EDTA.

These samples are provided by the AFSSA (Agence Française de Sécurité Sanitaire des Aliments) [French agency for food product safety], Lyon, FRANCE.

2. Detection of PrP$^{res}$ According to an ELISA-Type Method

Before use, the wells of the plates obtained according to example 2, point 2 above are presaturated by treatment with a mixture of skimmed milk (5%) and PBS/Tween 20 (0.05% w/v) at 37° C. for 60 minutes. The wells are then washed 3 times with 800 µl of PBS/Tween 20 (0.05% w/v) per well. The residual buffer is removed by turning the plates upside down.

100 µl of each sample of biological fluid prepared according to example 1, point 3 above, are distributed into the wells and the plate is incubated at 37° C. for 100 minutes with mechanical agitation at 400 rpm.

Following this first incubation, each well is rewashed three times with 800 µl of the PBS/Tween 20 (0.05% w/v) mixture and the plates are then dried.

The anti-PrP revealing antibody, labeled with peroxidase and diluted to 0.05 µg/ml in the PBS/Tween 20 (0.05% w/v) mixture, is added in a proportion of 100 µl per well and the plate is again incubated at 37° C. for 60 minutes. The antibody used recognizes the region defined by amino acids 145-154 of human PrP and the homologous regions of animal PrPs (antibody AC23).

The plate is then rinsed three times with 800 µl of a solution of PBS/Tween 20 (0.05% w/v) (PW41, Sanofi Pasteur) and the residual buffer is removed by turning the plate upside down.

The revelation is carried out by adding, to each well, 100 µl of a revealing solution prepared according to the manufacturer's recommendations (bioMérieux kit). The plate is incubated at room temperature in the dark for 10 minutes.

The reaction is stopped by adding 50 µl of a sulfuric acid solution (1.8N).

The signal obtained is read using a spectrophotometer at a wavelength of 490 nm (Spectrophotometer PR2100, Biorad).

3. Detection of PrP$^{res}$ in the Brain According to the Western Blotting Technique The protocol used corresponds to the reference protocol used for the diagnosis of certainty of prion diseases in animals and described by Madec et al, 2000, Microbiol pathogenesis, 28: 353-362.

4. Results

The results are given in table 1 below:

Table 1: Representation of the specificity of detection, by the ELISA-type method described above, of PrP$^{res}$ in the serum and the plasma of cattle, by comparison with the Western blotting-type reference protocol carried out using the brain from the same animals.

TABLE 1

| | | ELISA | | | |
|---|---|---|---|---|---|
| | | Serum | | Plasma | |
| | | Positive | Negative | Positive | Negative |
| Western blotting Brains | Positive | 6 | 0 | 3 | 0 |
| | Negative | 0 | 8 | 0 | 1 |

These results clearly show that the method of the invention makes it possible to detect PrP in biological fluids, because of the agreement between the two tests (method of the invention and reference Western blotting).

Moreover, the method of the invention is also applicable to physiological fluids such as sera and plasmas.

EXAMPLE 4

Application of the Method of the Invention to Various Species

1. Samples

Besides the samples used in example 3 above, positive ovine brain, serum and plasma samples derived from animals which were confirmed to be suffering from the prion disease scrapie by means of a search, by Western blotting, for PrP$^{res}$ in the brain tissue, and also plasmas from members of the ovine race infected with a BSE strain originating from bovine brains (counted as positive bovine) were used.

Murine serum samples were taken from C57BL6 mice which had been inoculated beforehand, by intraperitoneal injection, with 100 µl of a suspension of brain from a sheep suffering from a mouse-adapted C506M3 scrapie strain, at 10% in a solution of 5% glucose and diluted to 1/200. The blood was collected from the orbital sinus 15 days after inoculation.

These samples were also provided by the AFSSA (Agence Française de Sécurité Sanitaire des Aliments) [French agency for food product safety], Lyon, FRANCE.

2. Detection of PrP$^{res}$ in Biological Fluids According to an ELISA-Type Method The protocol described in example 3, point 2 above, was repeated.

3. Results

The results are reported in FIG. 1 giving the OD values obtained in positive or negative (+ or −) mouse serum, ovine serum and bovine plasma samples.

This figure demonstrates that, surprisingly, whatever the species considered, the optical density value for the samples derived from animals suffering from prion disease is significantly positive compared with the samples derived from control animals.

The method of the invention is therefore applicable to various species.

EXAMPLE 5

Use of Various Antibodies in the Method of the Invention

1. Samples

Bovine samples as described in example 3 above were used.

2. Detection of PrP$^{res}$ in Biological Fluids According to an ELISA-Type Method The protocol described in example 3, point 2 above, was repeated, using as revealing antibody either the antibody AC23 as described above, or the antibody 8D11G12 (bioMérieux, France).

3. Results

The results are reported in FIG. 2 giving the OD values obtained in positive or negative (+ or −) bovine plasma samples.

This figure demonstrates that the method of the invention can be carried out with various anti-PrP antibodies.

EXAMPLE 6

Detection of PrP$^{res}$ in Solid Organs

1. Samples

The samples used correspond:

i) to brain samples derived from positive or negative cattle which were confirmed to be suffering or not suffering from a prion disease by the conventional reference methods, including the search, by Western blotting, for PrP$^{res}$ in the brain tissue, and ii) to brains and spleens taken from mice already inoculated I/C with a mouse-adapted strain of scrapie and showing symptoms specific for the disease.

These samples were provided by the AFSSA (Agence Française de Sécurité Sanitaire des Aliments) [French agency for food product safety], Lyon, FRANCE.

They were treated as indicated in example 1, point 2 above.

2. Detection of PrP$^{res}$ in Solid Organs According to an ELISA-Type Method

The protocol described in example 3, point 2 above, was repeated.

3. Results

The results obtained on the same samples of solid organ by the reference Western blotting method were compared with those obtained by the method of the invention.

The results demonstrate that the use of the method of the invention combining both the use of streptomycin during preparation of the brains and use of a calixarene according to an ELISA-type method allowed the detection of PrP$^{res}$ in all the positive samples.

This use of the method of the invention also allows the detection of PrP$^{res}$ in the brains and spleens taken from mice inoculated with a mouse-adapted strain of scrapie.

EXAMPLE 7

Detection of PrP$^{res}$ in Human Serum and Plasma

1. Samples

The samples used correspond to plasma and serum samples taken from positive and negative patients confirmed as suffering or not suffering from Creutzfeldt-Jakob disease by the conventional reference methods.

2. Detection of PrP$^{res}$ in Serum and Plasma According to an ELISA-Type Method The protocol described in example 3, point 2 above, was repeated using, as revealing antibody, either the antibody AC23 as described above, or the antibody 8D11G12 (bioMérieux, France).

3. Results

The results are indicated in FIG. 3, which is a graphic representation giving the OD values obtained after detection, by means of the method of the invention, of PrP$^{res}$ in human serum and plasma samples positive with respect to Creutzfeldt-Jakob disease (CJD+) or negative (CJD−), using two different revealing antibodies.

FIG. 3 demonstrates that, surprisingly, the method of the invention allows the detection of PrP$^{res}$ specifically, in the serum and plasma of patients suffering from CJD.

The method of the invention is therefore also applicable to humans.

EXAMPLE 8

Use of Various Molecules Having at Least One Positive Charge and/or at Least One Glycosidic Bond 1. Preparation of the Samples The sample to be tested was prepared from BSE-positive bovine brain homogenate as follows:

1 µg of proteinase K was added to 100 µl of 10% homogenate of BSE-positive bovine brain suspended in a 5% glucose solution, and then which was incubated at 37° C. for one hour;

100 µl Laemmli buffer were then added, the mixture was vortexed, heated at 100° C. for 5 min, and centrifuged at 12 000 rpm for 5 minutes, and the supernatants were recovered.

Volumes of 5, 6, 8, 10 or 50 µl of this suspension, corresponding to 250, 300, 400, 500 or 2500 µg of brain tissue, were used for the experiments described below, with or without the addition of molecule having at least one positive charge and/or at least one glycosidic bond.

2. Western Blotting

After migration on a one-dimensional 15% polyacrylamide electrophoresis gel in the presence of sodium dodecyl sulfate (SDS PAGE) as described by Laemmli, Nature 227 (1970), 680-685, the proteins are transferred by electrophoresis onto nitrocellulose membranes and immunoblotted at room temperature for 60 minutes with a monoclonal antibody (Spi-Bio, France) that recognizes an epitope specific for the prion protein consisting of amino acids 146-160. The secondary detecting antibody (1/5000) is a goat antibody directed against mouse immunoglobulin heavy and light chains, conjugated to horseradish peroxidase (IgG H+L).

The blots are then washed and the signals are detected by chemiluminescence either with an ECL kit (Amersham) on films (Biomex light, Kodak) or with a super Signal Ultra (Pierce) and visualization on a Fluor S. Multimager (Bio-Rad).

3. Detection of PrP$^{sc}$ Using Dihydrostreptomycin Sesquisulfate

This molecule is a molecule having two guanidinium functions and one ammonium function.

Increasing concentrations (0, 2.5, 5 and 10 mg) of dihydrostreptomycin sesquisulfate, or of streptomycin by way of comparison, were added to a constant volume of PrP$^{sc}$ (50 µl) in the sample prepared in point 1 above.

After incubation at 37° C. for one hour, centrifugation was carried out at 12 000 rpm for 5 minutes and the supernatant (starting supernatant) was recovered.

The pellets are also recovered and 50 µl of a v/v solution of 8M urea and of Laemmli buffer are added thereto. After vigorous stirring with a vortex, they are heated at 100° C. for 5 minutes and centrifuged at 12 000 rpm for 5 minutes. Finally, the supernatants (pellet supernatant) were recovered.

The starting supernatants and also the pellet supernatants were migrated on SDS PAGE as indicated in point 2 above.

The results of this test are indicated in FIG. 4, giving a graphic representation of the electrophoresis gel obtained after migration and where the various lanes 1 to 15 correspond to the treatment conditions given in table 2 below, with or without the streptomycin-based molecules.

TABLE 2

| Lane | Treatment conditions | Supernatant concerned |
| --- | --- | --- |
| 1 | None; control | Starting supernatant |
| 2 | 2.5 mg of streptomycin | Starting supernatant |
| 3 | 5 mg of streptomycin | Starting supernatant |
| 4 | 10 mg of streptomycin | Starting supernatant |
| 5 | 2.5 mg of dihydrostreptomycin sesquisulfate | Starting supernatant |
| 6 | 5 mg of dihydrostreptomycin sesquisulfate | Starting supernatant |
| 7 | 10 mg of dihydrostreptomycin sesquisulfate | Starting supernatant |
| 8 | Molecular weight reference | None; reference |
| 9 | None; control | Pellet supernatant |
| 10 | 2.5 mg of streptomycin | Pellet supernatant |
| 11 | 5 mg of streptomycin | Pellet supernatant |
| 12 | 10 mg of streptomycin | Pellet supernatant |
| 13 | 2.5 mg of dihydrostreptomycin sesquisulfate | Pellet supernatant |
| 14 | 5 mg of dihydrostreptomycin sesquisulfate | Pellet supernatant |
| 15 | 10 mg of dihydrostreptomycin sesquisulfate | Pellet supernatant |

As indicated in FIG. 4, in the absence of the molecules tested, all the PrP$^{sc}$ bands are identified as being in the supernatant and, in the presence of streptomycin or dihydrostreptomycin sesquisulfate, the PrP$^{sc}$ material is found in the pellet.

The results show that dihydrostreptomycin sesquisulfate, like streptomycin, added to the medium, induces crosslinking of PrP which allows complete precipitation thereof with a simple centrifuge (no need for ultracentrifugation). The aggregates thus obtained can allow the detection of PrP, where appropriate after reaction with a ligand other than a protein ligand, according to the method of the invention.

4. Detection of PrP$^{sc}$ Using Triethylenetetramine or TET

This molecule is a molecule having four ammonium functions.

For this experiment, increasing concentrations of TET (105, 210, 420, 630 and 840 µg) were added to constant volumes (5 µl) of PrP$^{sc}$ obtained from 250 µg of brain from a bovine animal suffering from BSE, prepared according to point 1 above. The mixture was immediately centrifuged at 12 000 rpm for 5 minutes and the supernatant was used for immunodetection by Western blotting.

The results are indicated in FIG. 5, giving a graphic representation of the electrophoresis gel obtained after migration, where the various lanes 1 to 7 correspond to the treatment conditions given in table 3 below, with or without TET.

TABLE 3

| Lane | Treatment condition |
| --- | --- |
| 1 | No treatment; control |
| 2 | 105 µg of TET |
| 3 | 210 µg of TET |
| 4 | 420 µg of TET |
| 5 | 630 µg of TET |
| 6 | 840 µg of TET |
| 7 | Molecular weight reference |

The results in FIG. 5 show that the increase in the amount of triethylenetetramine in the medium through the addition of 105, 210, 420, 630 and 840 µg spontaneously induces an increase in the apparent molecular mass of the prion protein compared to a control without molecule. Thus, the detection of the prion protein is proportional to the amount of triethylenetetramine added. These results confirm that TET produces the same effects as streptomycin on PrP, under the conditions tested, i.e. a crosslinking of PrP proportional to the dose of TET, objectified by the increase in apparent molecular weight of the bands having migrated in the acrylamide gel.

5. Detection of $PrP^{sc}$ Using bis-3-aminopropylamine

This molecule is a molecule having three ammonium functions. The procedure described in point 3 above was repeated, with the exception that increasing amounts of bis-3-aminopropylamine (130, 260, 520, 780 and 1040 µg) were added to constant volumes (5 µl) of $PrP^{sc}$ in the sample prepared in point 1 above, and the mixture was incubated for 30 min at room temperature.

The results are indicated in FIG. 6, giving a graphic representation of the electrophoresis gel obtained after migration of the pellet supernatant, and where the various lanes 1 to 7 correspond to the treatment conditions given in table 4 below, with or without bis-3-aminopropylamine.

TABLE 4

| Lane | Treatment condition |
| --- | --- |
| 1 | Molecular weight reference |
| 2 | No treatment; control |
| 3 | 130 µg of bis-3-aminopropylamine |
| 4 | 260 µg of bis-3-aminopropylamine |
| 5 | 520 µg of bis-3-aminopropylamine |
| 6 | 780 µg of bis-3-aminopropylamine |
| 7 | 1040 µg of bis-3-aminopropylamine |

The results indicated in FIG. 6 show that the increase in the amount of bis-3-aminopropylamine in the medium through the addition of 130, 260, 520, 780 and 1040 µg induces an increase in the apparent molecular mass of the 3 prion protein bands compared to a control without molecule. Under these conditions, the prion protein precipitates under the centrifugation conditions mentioned in the previous points, which also corroborates effects similar to those produced by streptomycin.

6. Conclusion

The results show that the tested molecules added to the medium induce crosslinking of PrP, which allows complete precipitation thereof with a simple centrifuge.

The aggregates thus obtained can allow the detection of PrP, where appropriate after reaction with a ligand other than a protein ligand according to the method of the invention.

EXAMPLE 9

Detection of $PrP^{res}$ in Bovine Brain by Western Blotting, by Treatment of the Sample with the Calixarene C6S and with Streptomycin The samples used correspond to brain samples derived from positive bovine animals which were confirmed to be suffering from a prion disease by the conventional reference methods, including the search, by Western blotting, for $PrP^{res}$ in the brain tissue.

The organs are first of all homogenized in a 5% (w/v) glucose solution in order to obtain a 10% suspension.

1 μl of a 0.1M solution of calixarene C6S is added to 100 μl of the homogenized solution described above, and the mixture is then vortexed and incubated for one hour at 37° C.

7 μl of a 2 mg/l solution of proteinase K (PK) are added and the mixture is vortexed and then incubated at 37° C. for 30 minutes.

20 μl of a solution containing an increasing concentration of streptomycin sulfate (5%, 10% and 20%) are added, and the mixture is stirred and then reincubated at 37° C. for 1 hour.

After having added 100 μl of denaturing Laemmli buffer, the mixture is heated at 100° C. for 5 min and centrifuged at 12 000 rpm for 5 min. The supernatants are discarded and the pellets are recovered. 50 μl of a 50% v/v solution of 8M urea and Laemmli buffer are added thereto.

After vigorous vortexing, the mixture is heated at 100° C. for 5 min and centrifuged at 12 000 rpm for 5 min, and the supernatants are then recovered so as to migrate them on SDS-PAGE as described by Laemmli, Nature 227 (1970), 680-685.

After migration, the proteins are transferred by electrophoresis onto nitrocellulose membranes and immunoblotted at ambient temperature for 60 min with a monoclonal antibody that recognizes a specific epitope consisting of amino acids 126-160 (Spi-Bio, France). The secondary antibody (1/5000) is a goat antibody directed against mouse immunoglobulin heavy and light chains, conjugated to horseradish peroxidase (IgG H+L). The blots are then washed and the signals are detected by chemiluminescence either with an ECL kit (Amersham) on films (Biomex light, Kodak) or with a super Signal Ultra (Pierce) and visualization on a Fluor S. Multimager (BioRad).

The results are given in FIG. 7, in which lanes 1 to 3 correspond to the control samples not treated with the calixarene and streptomycin, lanes 4 to 6 correspond to the samples treated with the calixarene alone (treatment according to the procedure above, but without the streptomycin treatment step) and lanes 7 to 15 correspond to the samples treated with the calixarene, and then with streptomycin in a proportion of 5% (lanes 7 to 9), 10% (lanes 10 to 12) and 20% (lanes 13 to 15).

The results demonstrate that the detection of $PrP^{res}$ is improved by using calixarene and streptomycin together, and that the sensitivity of this method increases with the amount of streptomycin used.

EXAMPLE 10

Detection of $PrP^{res}$ in a Biological Fluid by Western Blotting, by Treatment of the Sample with Heparin and with Streptomycin 1. Samples 1.1: Preparation of Spleen Extracts for the Production of a Positive and Negative Standard The spleen extracts were prepared from autopsy samples of spleen from a patient who had died from new-variant-type Creutzfeldt-Jakob disease, and from a patient not suffering from Creutzfeldt-Jakob disease (CJD).

The spleen samples were first of all homogenized in a lysis buffer (0.5% NP-40 (Nonidet P-40)+0.5% DOC (sodium deoxycholate)) in order to obtain a 10% suspension.

The homogenates thus obtained were then centrifuged at 500 g for 5 minutes in order to remove the cell debris. The supernatants were conserved for the overloading of the blood samples.

1.2: Treatment of the Blood Samples

A pool of several bloods, taken from patients not suffering from Creutzfeldt-Jakob disease (normal donors), and brought into contact with a glycosaminoglycan, in this case heparin in the form of the lithium salt thereof, is prepared.

1.3: Production and Treatment of Samples Overloaded with the Positive and Negative Standard 1.3.1: Overloading The pool of blood, pretreated with heparin, was distributed into several aliquots so as to overload each aliquot with a different concentration of spleen homogenate positive or negative for CJD (1%, 5% and 10%) (v/v), according to the amounts indicated in table 5 below.

TABLE 5

| Overload concentration | Volume of homogenate added (µl) | Volume of plasma (µl) |
|---|---|---|
| Plasma control | 0 | 2150 |
| 1% | 12.5 | 1235 |
| 5% | 62.5 | 1185 |
| 10% | 125 | 1125 |

1.3.2: Digestion with Proteinase K

After overloading, the samples were digested with proteinase K (PK) according to a final concentration range of between 0 and 300 µg/ml (0-50-100-200 and 300 µg/ml in 250 µl of sample). After vortexing, the samples were incubated in an incubator for 30 minutes at 37° C.

1.3.3: Incubation with Streptomycin

25 µl of streptomycin (Gibco) at 1 g/ml (in distilled water) were then added to the mixture (final concentration of 200 mg/ml) and then, after homogenization with a vortex, the samples were incubated for 60 minutes in an incubator at 37° C.

1.3.4: Preparation for the Western Blotting

At the end of the incubation, the samples were centrifuged for 10 minutes at 15 000 rpm and the supernatants were removed.

The pellet was redissolved in 50 µl of SDS denaturing buffer and, after heating for 10 minutes at 100° C., the samples were again centrifuged for 5 minutes at 12 000 rpm. The supernatants were taken for analysis by Western blotting.

2. Detection of PrP$^{res}$ in the Overloaded Blood According to the Western Blotting Technique 2.1: Electrophoretic Migration and Transfer 15 µl of each supernatant were loaded onto a 12% bis-trisacrylamide gel (NuPage, Invitrogen). The migration is carried out at 200 volts for 45 minutes and the proteins are then transferred onto a PVDF membrane that has been rehydrated using the semi-dry system (graphite electrodes) for 1 hour at 21 volts, 110 milliamps and 2 watts.

2.2: Immunovisualization

The membrane was then treated according to the following steps:
saturation of the membrane in PBS-0.05% Tween (PBST)+ 5% milk
incubation overnight at +(2-8)° C.
rinsing of the membrane in PBST
addition of the primary antibody: 3F4 (Proteogenix, 9620.103), used at 0.2 µg/ml in PBST
incubation for 1 hour at ambient temperature (AT)
washes in PBST
addition of the second antibody: peroxidase-coupled anti-mouse (Jackson, 115-035-062), used diluted to 1/20 000 in PBS
incubation for 30 min at ambient temperature
washes in PBST
washes in PBS, pH 7.2
impregnation with an autoradiographic substrate (Super Signal, Pierce)
photographic development 3. Results The results are given in FIGS. 8 to 10, FIG. 8 corresponding to the diagrammatic representation (FIG. 8A) of the electrophoresis gel (FIG. 8B) following the Western blotting, obtained after migration of the normal samples overloaded with 1% of CJD+ or CJD− spleen homogenate, FIG. 9 corresponding to the diagrammatic representation (FIG. 9A) of the electrophoresis gel (FIG. 9B) following the Western blotting, obtained after migration of the normal samples overloaded with 5% of CJD+ or CJD− spleen homogenate, and FIG. 10 corresponding to the diagrammatic representation (FIG. 10A) of the electrophoresis gel (FIG. 10B) following the Western blotting, obtained after migration of the normal samples overloaded with 10% of CJD+ or CJD− spleen homogenate.

On these gels, the samples in lanes 1 to 5 and lanes 8 to 12 have the characteristics indicated in table 6 below, lane 6 corresponds to the molecular weight marker lane and lane 7 corresponds to the positive control sample obtained from an extract of brain from a patient who had died from Creutzfeldt-Jakob disease, prepared according to the reference technique used routinely for the diagnosis of certainty of CJD (Madec et al., 2000, Microbiol. Pathogenesis, 28:353-362).

TABLE 6

| Lanes | Overload source | PK (µg/ml) | Deposit volume (µl) |
|---|---|---|---|
| 1 | CJD+ spleen | 0 | 15 |
| 2 |  | 50 |  |
| 3 |  | 100 |  |
| 4 |  | 200 |  |
| 5 |  | 300 |  |
| 8 | CJD− spleen | 0 | 15 |
| 9 |  | 50 |  |
| 10 |  | 100 |  |
| 11 |  | 200 |  |
| 12 |  | 300 |  |

The results demonstrate a proteinase K-resistant band in the blood sample overloaded with spleen homogenate positive for CJD, whatever the overload density. In fact, this band remains visible whatever the concentration of proteinase K for the positive sample, whereas it disappears when the concentration of PK is greater than 100 µg/ml for the negative sample (overloaded with CJD(−) spleen).

Thus, the realization of the test with the combined use of heparin and of streptomycin confirms the sensitivity and the specificity of detection of PrP$^{res}$ of lymphoid origin (spleen) in blood samples.

This corresponds well to the physiopathological situation in which a test is carried out for detection of PrP$^{res}$ in the blood of individuals contaminated with the pathogenic prion (PrP$^{sc}$), taken before the neuroinvasion phase and/or the first clinical manifestations of the disease.

This is the context in which a screening of blood donations from contaminated individuals, who are normal carriers and/or in the sub-clinical phase, finds its use in public health.

The invention claimed is:

1. A method for detecting PrP in a biological sample of human or animal origin that may contain said PrP, comprising:
   a) contacting the biological sample with a molecule selected from the group consisting of polyallylamine, triethylenetetraamine (TET), bis-3-aminopropylamine, spermine tetrahydrochloride, dihydrostreptomycin sesquisulfate, streptomycin, and salts of streptomycin to form PrP aggregates in a reaction mixture;

b) adding to the sample a macrocyclic ligand having general formula (I):

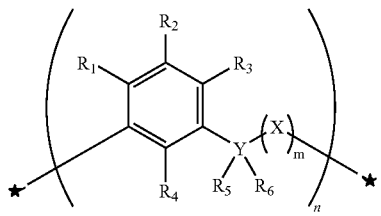

where:
- $R_1$ represents a hydrogen atom, a hydroxyl group, an OR group or an OCOR group, R being as defined below,
- $R_2$ represents a hydrogen atom or an R, COR, Pol or $CH_2Pol$ group, in which Pol represents a phosphate, sulfate, amine, ammonium or carboxylic acid group, and R is as defined below,
- $R_3$ represents a hydrogen atom, a hydroxyl group, an OR group or an OCOR group in which R is as defined below,
- $R_4$ represents a hydrogen atom, a hydroxyl group, an OR group, an $OCH_2R$ group or an OCOR group, in which R is as defined below,
- Y is a carbon, nitrogen or sulfur atom,
- $R_5$ and $R_6$ each independently are absent or represent a hydrogen atom, a $CH_2$ group or an R group as defined below, or else $R_5$ and $R_6$ together represent an oxygen or sulfur atom,
- X represents a $CH_2$ group, or an oxygen or sulfur atom,
- m represents an integer equal to 0 or 1,
- R represents a hydrogen atom or a saturated or unsaturated, branched or unbranched, cyclic or noncyclic hydrocarbon-based chain which may or may not be substituted with a halogen group, and which carries polar or nonpolar functions,
- n is an integer between 3 and 15, and
- the substituents $R_1$ to $R_5$, R, X and Y and the integer m may be different in nature according to the units; and c) detecting the presence of PrP.

2. The method of claim 1, wherein (a) is performed before (b).

3. The method of claim 1, further comprising adding proteinase K to the sample.

4. The method of claim 1, further comprising:
adding proteinase K to the sample to digest $PrP^c$ before (a); and
detecting the presence of PrP thereby detecting the presence of $PrP^{res}$.

5. The method of claim 1, further comprising between (b) and (c):
separating the PrP aggregates from the reaction mixture, and
denaturing the PrP aggregates.

6. The method of claim 1, wherein detecting the presence of PrP comprises contacting the PrP with a PrP-specific binding partner for an immunoreaction between the PrP-specific binding partner and the PrP.

7. The method of claim 1, wherein the macrocyclic ligand is bound to a solid support.

8. The method of claim 1, wherein the macrocyclic ligand corresponds to general formula (Ia) below:

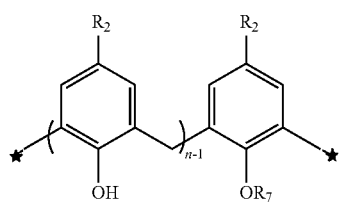

where:
- n is an integer between 4 and 8,
- each group $R_2$, taken independently, is a sulfate group or a phosphate group, and
- $R_7$ represents a $(CH_2)_t$—$(CO)_s$—$(NH_2)$ group or a $(CH_2)_t$—COOH group where t is an integer between 0 and 6 and s is an integer between 0 and 6.

9. The method of claim 8, wherein said ligand is a calixarene of formula (Ia) where:
- the two $R_2$ groups are each a sulfate group,
- n is 4, 6 or 8, and
- $R_7$ is a hydrogen atom, a —$CH_2COOH$ group, a —$CH_2CONH_2$ group, or a —$CH_2CH_2NH_2$ group.

10. The method of claim 8, where:
- the two $R_2$ groups are each a sulfate group,
- n=6, and
- $R_7$ is —$CH_2CH_2NH_2$.

11. The method of claim 1, wherein the molecule of (a) is streptomycin.

12. The method of claim 1, wherein the molecule of (a) is a salt of streptomycin.

* * * * *